(12) United States Patent
Pilgeram

(10) Patent No.: US 12,171,422 B2
(45) Date of Patent: *Dec. 24, 2024

(54) SOFT TISSUE FIXATION DEVICE AND METHODS

(71) Applicant: Howmedica Osteonics Corp., Mahwah, NJ (US)

(72) Inventor: Kyle Craig Pilgeram, San Jose, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 350 days.

This patent is subject to a terminal disclaimer.

(21) Appl. No.: 16/875,204

(22) Filed: May 15, 2020

(65) Prior Publication Data

US 2020/0345340 A1  Nov. 5, 2020

Related U.S. Application Data

(63) Continuation of application No. 15/808,382, filed on Nov. 9, 2017, now Pat. No. 10,653,410, which is a
(Continued)

(51) Int. Cl.
*A61B 17/16* (2006.01)
*A61B 17/04* (2006.01)
(Continued)

(52) U.S. Cl.
CPC ...... *A61B 17/0401* (2013.01); *A61B 17/0482* (2013.01); *A61B 17/0487* (2013.01);
(Continued)

(58) Field of Classification Search
CPC ............ A61B 17/1631; A61B 17/7208; A61B 17/8897
See application file for complete search history.

(56) References Cited

U.S. PATENT DOCUMENTS 749,624 A   1/1904  McCullough
1,308,798 A   7/1919  Masland
(Continued)

FOREIGN PATENT DOCUMENTS

DE  3131496 A1  2/1983
DE  4231101 A1  3/1994
(Continued)

OTHER PUBLICATIONS

BIOMET Sports Medicine: Micromax Flex Suture Anchor, (2008).
(Continued)

*Primary Examiner* — Samuel S Hanna
(74) *Attorney, Agent, or Firm* — Lerner David LLP

(57) ABSTRACT

Filamentary fixation devices may be used in a variety of surgical procedures to secure soft tissue to bone. The present invention provides various devices, systems, kits and instrumentation for performing such surgical procedures including preparation of soft tissue and bone, preparation and manipulation of such filamentary fixation devices, and insertion and utilization of the fixation devices within a patient's anatomy. In one embodiment, a method for securing soft tissue to bone, the method includes accessing the soft tissue and the bone, passing a filament through the soft tissue, preparing a bore hole in the bone, loading the filament into a filamentary fixation device, implanting the filamentary fixation device, with the filament, into the bore hole, and tensioning the filament so that the filamentary fixation device and filament are secured within the bore hole.

12 Claims, 14 Drawing Sheets

Related U.S. Application Data continuation of application No. 14/339,007, filed on Jul. 23, 2014, now Pat. No. 10,123,792, which is a continuation of application No. 13/588,586, filed on Aug. 17, 2012, now abandoned.

(60) Provisional application No. 61/679,336, filed on Aug. 3, 2012.

(51) Int. Cl.
| | |
|---|---|
| *A61B 17/17* | (2006.01) |
| *A61B 17/00* | (2006.01) |
| *A61B 50/00* | (2016.01) |
| *F16C 1/00* | (2006.01) |
| *F16C 1/02* | (2006.01) |

(52) U.S. Cl.
CPC ...... *A61B 17/1615* (2013.01); *A61B 17/1631* (2013.01); *A61B 17/1684* (2013.01); *A61B 17/17* (2013.01); *A61B 17/1742* (2013.01); *A61B 17/1796* (2013.01); *A61B 2017/00482* (2013.01); *A61B 2017/0053* (2013.01); *A61B 2017/0409* (2013.01); *A61B 2017/0414* (2013.01); *A61B 2017/0496* (2013.01); *A61B 17/1633* (2013.01); *A61B 17/1666* (2013.01); *A61B 17/1714* (2013.01); *A61B 17/1778* (2016.11); *A61B 2050/0055* (2016.02); *F16C 1/00* (2013.01); *F16C 1/02* (2013.01)

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,461,947 A | 2/1949 | Weber |
| 2,515,365 A | 7/1950 | Zublin |
| 2,547,571 A | 4/1951 | Ettinger |
| 2,773,672 A | 12/1956 | Holmes et al. |
| 2,808,632 A | 10/1957 | Cline |
| 2,833,284 A | 5/1958 | Springer |
| 3,384,085 A | 5/1968 | Hall |
| 3,407,889 A | 10/1968 | Hjalsten et al. |
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,824 A | 6/1995 | Akerfeldt et al. |
| 5,423,860 A | 6/1995 | Lizardi et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,617 A | 12/1996 | Houser |

(56) References Cited

U.S. PATENT DOCUMENTS

| | | |
|---|---|---|
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,658,313 A | 8/1997 | Thal |
| 5,662,658 A | 9/1997 | Wenstrom, Jr. |
| 5,664,914 A | 9/1997 | Taniguchi |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,315 A | 10/1997 | Szabo |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,677 A | 11/1997 | Schmieding et al. |
| 5,695,513 A | 12/1997 | Johnson et al. |
| 5,699,657 A | 12/1997 | Paulson |
| 5,707,374 A | 1/1998 | Schmidt |
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,530 A | 3/1998 | Popken |
| 5,725,541 A | 3/1998 | Anspach et al. |
| 5,728,136 A | 3/1998 | Thal |
| 5,732,606 A | 3/1998 | Chiang |
| 5,733,306 A | 3/1998 | Bonutti |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,788,699 A | 8/1998 | Bobst et al. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,895,179 A | 4/1999 | Gschwend et al. |
| 5,897,574 A | 4/1999 | Bonutti |
| 5,906,626 A | 5/1999 | Carrillo |
| 5,908,423 A | 6/1999 | Kashuba et al. |
| 5,921,986 A | 7/1999 | Bonutti |
| 5,928,244 A | 7/1999 | Tovey et al. |
| 5,941,139 A | 8/1999 | Vodehnal |
| 5,941,883 A | 8/1999 | Sklar |
| 5,947,659 A | 9/1999 | Mays |
| 5,948,002 A | 9/1999 | Bonutti |
| 5,951,559 A | 9/1999 | Burkhart |
| 5,968,078 A | 10/1999 | Grotz |
| 5,970,697 A | 10/1999 | Jacobs et al. |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,030,406 A | 2/2000 | Davis et al. |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,083,522 A | 7/2000 | Chu et al. |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,258,093 B1 | 7/2001 | Edwards et al. |
| 6,270,501 B1 | 8/2001 | Freiberg et al. |
| 6,306,138 B1 | 10/2001 | Clark et al. |
| 6,312,438 B1 | 11/2001 | Adams |
| 6,343,482 B1 | 2/2002 | Endo et al. |
| 6,352,538 B2 | 3/2002 | McGuire et al. |
| 6,358,253 B1 | 3/2002 | Torrie et al. |
| 6,361,537 B1 * | 3/2002 | Anderson .......... A61B 17/8047 606/294 |
| 6,364,886 B1 | 4/2002 | Sklar |
| 6,383,188 B2 | 5/2002 | Kuslich et al. |
| 6,416,517 B2 | 7/2002 | Harder et al. |
| 6,419,678 B1 | 7/2002 | Asfora |
| 6,419,684 B1 | 7/2002 | Heisler et al. |
| 6,431,801 B2 | 8/2002 | Vasudeva et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,474,425 B1 | 11/2002 | Truax et al. |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,730,092 B2 | 5/2004 | Songer |
| 6,740,090 B1 | 5/2004 | Cragg et al. |
| 6,746,451 B2 | 6/2004 | Middleton et al. |
| 6,780,188 B2 | 8/2004 | Clark et al. |
| 6,783,533 B2 | 8/2004 | Green et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,874,978 B2 | 4/2005 | Gongola |
| 6,878,150 B1 | 4/2005 | McGuire et al. |
| 6,887,259 B2 | 5/2005 | Lizardi |

(56) References Cited

U.S. PATENT DOCUMENTS

| | | |
|---|---|---|
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,018,144 B2 | 3/2006 | Sasagawa et al. |
| 7,025,770 B2 | 4/2006 | McGuire et al. |
| 7,029,479 B2 | 4/2006 | Tallarida et al. |
| 7,029,490 B2 | 4/2006 | Grafton et al. |
| 7,041,107 B2 | 5/2006 | Pohjonen et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,235 B2 | 2/2011 | Ellis |
| 7,892,256 B2 | 2/2011 | Grafton et al. |
| 7,901,431 B2 | 3/2011 | Shurnas |
| 7,905,903 B2 | 3/2011 | Stone et al. |
| 7,905,904 B2 | 3/2011 | Stone et al. |
| 7,909,547 B2 | 3/2011 | Jordan et al. |
| 7,909,851 B2 | 3/2011 | Stone et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,963,967 B1 | 6/2011 | Woods |
| 7,981,117 B2 | 7/2011 | Newton et al. |
| 7,981,140 B2 | 7/2011 | Burkhart |
| 7,993,369 B2 | 8/2011 | Dreyfuss |
| 8,002,733 B2 | 8/2011 | Kraft et al. |
| 8,043,253 B2 | 10/2011 | Kraft et al. |
| 8,057,500 B2 | 11/2011 | Mitusina |
| 8,070,750 B2 | 12/2011 | Wenstrom, Jr. et al. |
| 8,088,130 B2 | 1/2012 | Kaiser et al. |
| 8,109,700 B2 | 2/2012 | Jordan et al. |
| 8,114,088 B2 | 2/2012 | Miller |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,312,942 B2 | 11/2012 | Ho et al. |
| 8,317,825 B2 | 11/2012 | Stone |
| 8,337,525 B2 | 12/2012 | Stone et al. |
| 8,361,113 B2 | 1/2013 | Stone et al. |
| 8,366,713 B2 | 2/2013 | Long et al. |
| 8,394,129 B2 | 3/2013 | Morgenstern Lopez et al. |
| 8,398,678 B2 | 3/2013 | Baker et al. |
| 8,409,253 B2 | 4/2013 | Stone et al. |
| 8,439,976 B2 | 5/2013 | Albertorio et al. |
| 8,469,998 B2 | 6/2013 | Sojka et al. |
| 8,512,340 B2 | 8/2013 | Easley et al. |
| 8,518,087 B2 | 8/2013 | Lopez et al. |
| 8,556,911 B2 | 10/2013 | Mehta et al. |
| 8,562,645 B2 | 10/2013 | Stone et al. |
| 8,591,578 B2 | 11/2013 | Albertorio et al. |
| 8,597,333 B2 | 12/2013 | Morgenstern Lopez et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,986,327 B2 | 3/2015 | Karasic et al. |
| 9,072,530 B2 | 7/2015 | Mehta et al. |
| 9,173,652 B2 | 11/2015 | Lombardo et al. |
| 9,463,011 B2 | 10/2016 | Dreyfuss et al. |
| 2002/0019635 A1 | 2/2002 | Wenstrom et al. |
| 2002/0087166 A1 | 7/2002 | Brock et al. |
| 2002/0183758 A1 | 12/2002 | Middleton et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0049194 A1 | 3/2004 | Harvie et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193168 A1 | 9/2004 | Long et al. |
| 2004/0193217 A1 | 9/2004 | Lubbers et al. |
| 2004/0208717 A1 | 10/2004 | Greenhalgh |
| 2004/0260300 A1 | 12/2004 | Gorensek et al. |
| 2004/0267277 A1 | 12/2004 | Zannis et al. |
| 2004/0267317 A1 | 12/2004 | Higgins et al. |
| 2005/0015153 A1 | 1/2005 | Goble et al. |
| 2005/0033362 A1 | 2/2005 | Grafton |
| 2005/0038427 A1 | 2/2005 | Perriello et al. |

(56) References Cited

U.S. PATENT DOCUMENTS

| | | |
|---|---|---|
| 2005/0070906 A1 | 3/2005 | Clark et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203519 A1* | 9/2005 | Harms ............... A61B 17/7026 606/279 |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0261604 A1 | 11/2005 | Stephens et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0015110 A1 | 1/2006 | Pepper |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247642 A1 | 11/2006 | Stone et al. |
| 2006/0259043 A1 | 11/2006 | Miyamoto et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0185532 A1 | 8/2007 | Stone et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2007/0288031 A1 | 12/2007 | Dreyfuss et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0065114 A1 | 3/2008 | Stone et al. |
| 2008/0071282 A1 | 3/2008 | Assell et al. |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140092 A1 | 6/2008 | Stone et al. |
| 2008/0140093 A1 | 6/2008 | Stone et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0147071 A1 | 6/2008 | Serra et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0243163 A1 | 10/2008 | Masseglia et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |
| 2008/0275453 A1 | 11/2008 | Lafosse et al. |
| 2008/0306483 A1 | 12/2008 | Iannarone |
| 2008/0306511 A1 | 12/2008 | Cooper et al. |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0112270 A1 | 4/2009 | Lunn et al. |
| 2009/0112770 A1 | 4/2009 | Schmidt et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0157124 A1 | 6/2009 | Ferragamo et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0318961 A1 | 12/2009 | Stone et al. |
| 2009/0326538 A1 | 12/2009 | Sennett et al. |
| 2010/0042104 A1* | 2/2010 | Kota ................. A61B 17/1631 606/79 |
| 2010/0049196 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0262146 A1 | 10/2010 | Tulkis |
| 2010/0268275 A1 | 10/2010 | Stone et al. |
| 2010/0286694 A1 | 11/2010 | Rio et al. |
| 2010/0292731 A1 | 11/2010 | Gittings et al. |
| 2010/0292732 A1 | 11/2010 | Hirotsuka et al. |
| 2010/0292792 A1 | 11/2010 | Stone et al. |
| 2010/0305709 A1 | 12/2010 | Metzger et al. |
| 2010/0324608 A1 | 12/2010 | Albertorio et al. |
| 2011/0004243 A1 | 1/2011 | Dreyfuss |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0034764 A1* | 2/2011 | Verbeek ............. A61B 1/00071 600/101 |
| 2011/0046625 A1 | 2/2011 | Boileau et al. |
| 2011/0054526 A1 | 3/2011 | Stone et al. |

(56) References Cited

U.S. PATENT DOCUMENTS

| | | |
|---|---|---|
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1 | 4/2011 | Kaiser et al. |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053629 A1 | 3/2012 | Reiser et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0160050 A1 | 6/2012 | Nishio et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203231 A1 | 8/2012 | Long et al. |
| 2012/0203288 A1 | 8/2012 | Lange et al. |
| 2012/0209325 A1 | 8/2012 | Gagliano et al. |
| 2012/0245585 A1 | 9/2012 | Kaiser et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0116730 A1 | 5/2013 | Denham et al. |
| 2013/0131722 A1 | 5/2013 | Marchand et al. |
| 2013/0158596 A1 | 6/2013 | Miller et al. |
| 2013/0158601 A1 | 6/2013 | Stone et al. |
| 2013/0165972 A1 | 6/2013 | Sullivan |
| 2013/0190818 A1 | 7/2013 | Norton |
| 2013/0190819 A1 | 7/2013 | Norton |
| 2013/0237997 A1 | 9/2013 | Arai et al. |
| 2013/0245700 A1 | 9/2013 | Choinski |
| 2013/0268000 A1 | 10/2013 | Harner et al. |
| 2013/0296864 A1* | 11/2013 | Burley ............... A61B 17/17 606/80 |
| 2013/0296931 A1 | 11/2013 | Sengun |
| 2013/0317544 A1 | 11/2013 | Ferguson et al. |
| 2013/0325063 A1 | 12/2013 | Norton et al. |
| 2013/0345749 A1 | 12/2013 | Sullivan et al. |
| 2014/0018816 A1* | 1/2014 | Fenn ............... B25B 23/0035 606/104 |
| 2014/0039503 A1 | 2/2014 | Pilgeram |
| 2014/0135835 A1 | 5/2014 | Stone et al. |
| 2014/0163679 A1 | 6/2014 | Re et al. |
| 2014/0188163 A1 | 7/2014 | Sengun |

FOREIGN PATENT DOCUMENTS

| | | |
|---|---|---|
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1174584 A2 | 1/2002 |
| EP | 1369089 A2 | 12/2003 |
| EP | 1398455 A2 | 3/2004 |
| EP | 2286742 A1 | 2/2011 |
| EP | 2544607 A1 | 1/2013 |
| EP | 2548519 A2 | 1/2013 |
| EP | 2596755 A2 | 5/2013 |
| FR | 1166884 A | 11/1958 |
| FR | 2606996 A1 | 5/1988 |
| FR | 2676638 A1 | 11/1992 |
| GB | 2093353 A | 9/1982 |
| NO | 0128457 A1 | 4/2001 |
| WO | 95011631 A1 | 5/1995 |
| WO | 9628100 A1 | 9/1996 |
| WO | 9704908 A1 | 2/1997 |
| WO | 9722301 A1 | 6/1997 |
| WO | 0024327 A2 | 5/2000 |
| WO | 0044291 A1 | 8/2000 |
| WO | 0160268 A1 | 8/2001 |
| WO | 03007861 A1 | 1/2003 |
| WO | 2004092531 A2 | 10/2004 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |
| WO | 2014107729 A2 | 7/2014 |

OTHER PUBLICATIONS

Burkinshaw, U.S. Appl. No. 60/418,545, filed Oct. 15, 2002.
Canadian Office Action for Application No. 2,811,838 dated May 22, 2014.
Charles McCartney, U.S. Appl. No. 13/792,982, filed Mar. 11, 2013, titled "Filamentary Fixation Device and Assembly and Method of Assembly, Manufacture and Use".
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.

(56) References Cited

OTHER PUBLICATIONS

Cole et al., American Journal of Sports Medicine, vol. XX, No. X, Apr. 2011, 10 pages.
Conmed: LINVATEC: Shoulder Restoration System Y-Knot 1.3mm All Suture Anchor, @ 2011 Linvatec Corporation, a subsidiary of ConMed Corporation—CBR 3057 (4 pages).
European Search Report for Application No. 13178933.1 dated Sep. 25, 15.
European Search Report, EP 10173568, dated Nov. 30, 2010.
Extended European Search Report for Application No. EP 12164104 dated Jul. 11. 2012.
Extended European Search Report for Application No. EP14157129 dated Oct. 9, 2014.
Extended European Search Report for Application No. EP14159656 dated Jun. 6, 2014.
HHS Tube, Fort Wayne Metals Research Products Corp., 2009, 2 pages.
International Search Report and Written Opinion for Application No. PCT/US2012/024303 dated May 24, 2012.
International Search Report and Written Opinion for Application No. PCT/US2014/021231 dated Jun. 25, 2014.
International Search Report and Written Opinion for Application No. PCT/US2014/069087 dated Jun. 17, 2015.
International Search Report PCT/US2010/042264, dated Sep. 30, 2010.
Long et al., U.S. Appl. No. 13/368,730, filed Feb. 8, 2012, titled "Flexible Microdrilling Instrumentation, Kits and Methods".
Marchand et al., U.S. Appl. No. 13/303,849, filed Nov. 23, 2011, titled "Filamentary Suture Anchor".
Medtronic, The VISAO High-Speed Otologic Drill Catalog, 2007, 12 pages.
Perthes, German Surgery Periodical, vol. 85, Commemmorative Publication, pp. 2-18, 1906.
Steiner et al., U.S. Appl. No. 13/085,882, filed Apr. 13, 2011, titled "Flexible Acl Instrumentation, Kit and Method".
Sugaya et al., Journal of Bone and Joint Surgery, vol. 85-A, No. 5, pp. 878-884, May 2003.

\* cited by examiner

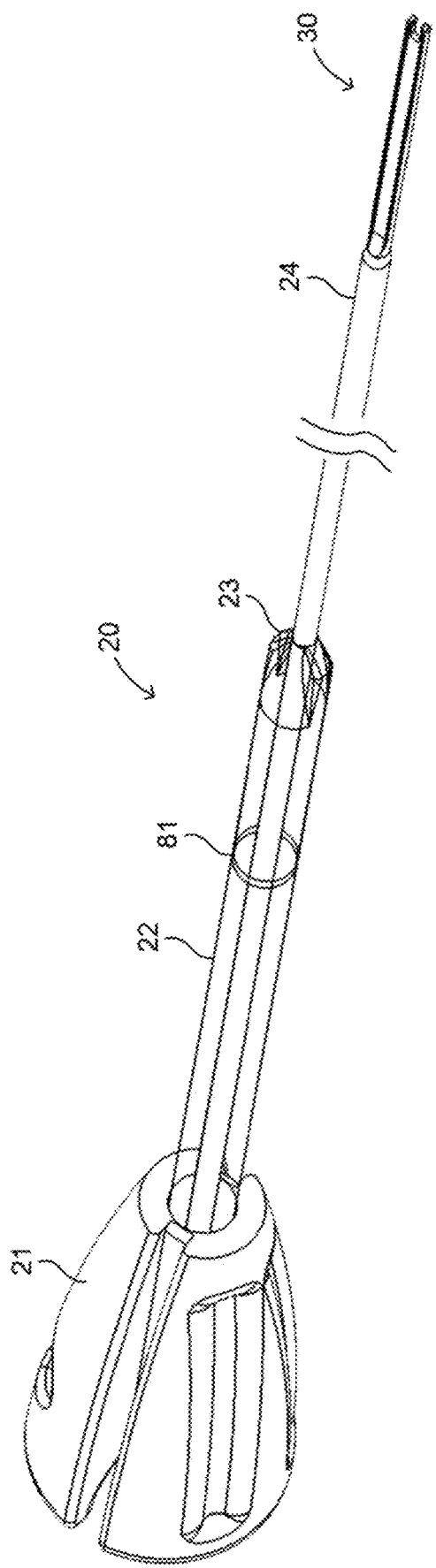
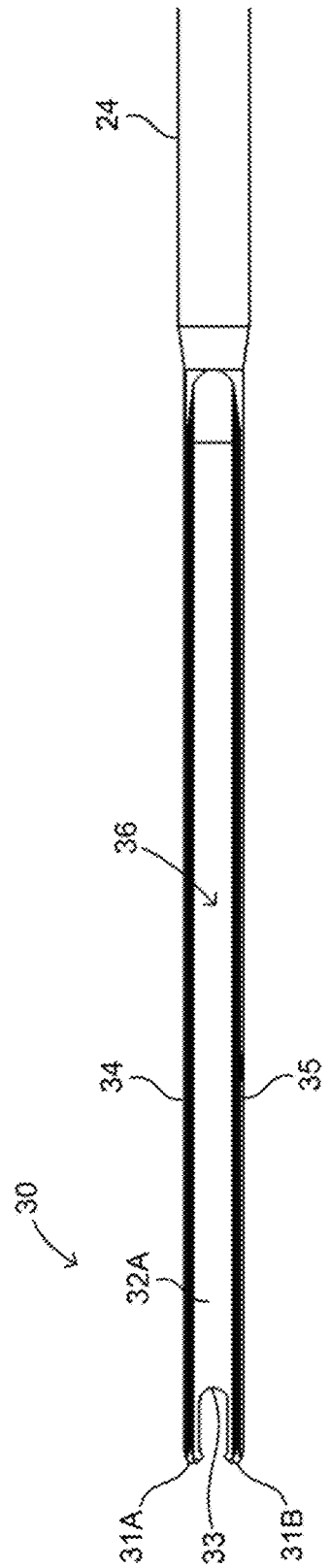
FIG. 3A
FIG. 3B

SOFT TISSUE FIXATION DEVICE AND METHODS

CROSS-REFERENCE TO RELATED APPLICATION

This application is a continuation of U.S. application Ser. No. 15/808,382, filed on Nov. 9, 2017 which is a continuation of U.S. application Ser. No. 14/339,007, filed on Jul. 23, 2014 which is a continuation of U.S. application Ser. No. 13/588,586 filed on Aug. 17, 2012, which claims the benefit of the filing date of U.S. Provisional Application No. 61/679,336 filed Aug. 3, 2012, the disclosures of which are hereby incorporated herein by reference.

BACKGROUND OF THE INVENTION

Traditional fixation devices, such as suture anchors or tissue anchors, are typically made of metal or hard plastic, and include a structure which connects or otherwise secures a filament, such as a suture, or a portion of tissue, to the body of the device. In certain applications, these devices have a diameter suitable to hold the devices within a bone. Such devices may also include additional structures to dig into the bone, such as wings, barbs, threads, or the like.

However, such traditional devices tend to be large in diameter, and must include sufficient material, or other additional structures, to withstand the forces pulling against the device, whether via a suture or directly against the device itself. The size of such devices may limit the possible implantation locations in the body, as sufficient bone mass is required to accommodate the device. Moreover, a large hole must be drilled into the bone to allow for passage of the device through the cortical layer and into the cancellous bone. The larger drill holes may be too invasive resulting in excessive loss of healthy bone, or creation of a large repair site.

A recent trend in fixation device technology is the "soft" device, also referred to as a "filamentary" fixation device, in which the device itself is constructed of a filamentary material. Such filamentary fixation devices may provide solutions to the various problems encountered with traditional devices, as summarized above.

BRIEF SUMMARY OF THE INVENTION

Such filamentary fixation devices may be used in a variety of surgical procedures to secure soft tissue to bone. The present invention provides various devices, systems, kits and instrumentation for performing such surgical procedures including preparation of soft tissue and bone, preparation and manipulation of such filamentary fixation devices, and insertion and utilization of the fixation devices within a patient's anatomy. Furthermore, the devices and instrumentation of embodiments of the present invention can be used in methods to perform knotless tissue repair procedures. The devices and instruments of embodiments of the present invention may provide for improved repairs of soft tissue including the ability to prepare and use smaller bore holes in bone, ability to perform methods of soft tissue repair in a less invasive manner, and the ability to perform such methods at various angles, approaches, and directions of entry, such that soft tissue injuries in difficult to reach anatomical locations may be more easily accessed.

In one embodiment, the present invention includes a system for the repair of soft tissue, the system including at least one instrument adapted to implant a filamentary fixation device into bone, and the filamentary fixation device. The system may further include at least one filament adapted to cooperate with the fixation device.

In another embodiment, the present invention includes a system for the repair of soft tissue, the system including a filamentary fixation device, an inserter, a guide, and a loading device. The inserter includes a distal portion for accommodating the filamentary fixation device, and an at least one groove extending along at least a portion of a length of the inserter from a distal-most end towards a proximal end. The guide is cannulated along at least a portion of its length and includes a distal tip including an engagement surface for engaging anatomy and a handle on a proximal end. The loading device may include a casing adapted to accommodate at least a portion of the filamentary fixation device and at least a portion of the inserter, and a channel extending from a first side of the casing to a second side of the casing.

Further, in another aspect of the above embodiment, the filamentary fixation device may be adapted to be positioned on the distal end of the inserter and within at least a portion of the channel of the loading device. The loading device may further include a second channel extending from the first side of the housing to a third side of the housing. The first and second channels may further follow routes within the housing. Further, the first and second channels may intersect along at least a portion of their lengths, and further may be circuitous or tortuous. The channels may further be sized to accommodate at least one of a threading filament and a filament therein. The threading filament may include a wire, a suture, or a combination of the wire and suture. The threading filament may be positioned within the first channel, the second channel, the filamentary fixation device, or any combination, and may further be adapted to thread the filament into the loading device.

In another aspect of this embodiment, the housing of the loading device may include two or more independent portions adapted to be positioned together or separated from one another in a hinged relationship, for example.

In yet another aspect of this embodiment of the present invention, the inserter may further include a second groove extending along at least a portion of the length of the inserter from the distal-most end towards the proximal end. The distal portion of the inserter may have an I-beam shape, wherein the filamentary fixation device is positioned within the first and second grooves and looped around or folded over a saddle at the distal-most end. The distal-most end of the inserter may be a forked end, a flat blade end, a flat blunt end, or the like. The inserter may include a handle at its proximal end. Further, portions of the inserter and guide shafts may form an abutment or stop structure. The guide may have a curve along at least a portion of its length, and the inserter may include a flexible portion and be adapted to pass through the cannula along the length of the guide and through the curved portion of the guide.

In a further aspect of this embodiment, the system may further include a drill having a drill head and a shaft. At least a portion of the shaft may be flexible and be adapted to pass through the cannula along the length of the guide and through the curved portion of the guide. The drill may further include a bushing positioned along at least a portion of the length of the shaft.

In another embodiment, the present invention may include a loading device for preparing a filamentary fixation device including a housing adapted to accommodate at least a portion of the filamentary fixation device, and a channel extending from a first side of the housing to a second side of the housing, and a second channel extending from the first side of the housing to a third side of the housing, wherein the first and second channels follow routes within the housing. Further, the first and second channels may intersect along at least a portion of their lengths. The channels may further be sized to accommodate a filament therein. The filament may be positioned within the first channel, the second channel, the filamentary fixation device, or any combination. The housing of the loading device may include two or more independent portions adapted to be positioned together or separated from one another. Additionally, the loading device may be adapted to accommodate at least a portion of an inserter, wherein the inserter can engage the filamentary fixation device within the loading device.

In yet another embodiment, the present invention may include a system for preparing a bone for fixation of soft tissue, the system including a guide and a drill having a bushing positioned thereon. The bushing may have a length, wherein at least a portion of the length may be compressible, expandable, or both. Specifically, the bushing may have at least one spring-like structure incorporated into its length, may be constructed of an elastic material, such as plastic or or the like, or may include at least one cut or slot, to create an elastic structure.

In another embodiment, the present invention includes a surgical instrument including an instrument body including a shaft having a distal end, a proximal end and a length therebetween and a bushing having a length, wherein at least a portion of the length of the bushing includes a spring portion including a resilient member, wherein the bushing is cannulated such that the shaft of the instrument is positioned therethrough. The bushing may further include a solid portion along at least a portion of the length, and alternatively, the bushing, along its length, may include more than one spring portion and more than one solid portion, each spring portion separated from one another by a solid portion. In another alternative, the spring portion may extend along the entire length of the bushing. The instrument of this embodiment may be a drill or an implant inserter. In the example of a drill, having a distal drilling tip, the bushing may be positioned on the shaft of the drill adjacent to the distal drilling tip. The instrument of this embodiment may be positioned through a cannulated guide, the guide may have a length and a curved portion along at least a portion of its length, wherein the bushing and shaft of the instrument may be adapted to pass through the curved portion of the cannulated guide. The bushing further has an outer diameter sufficient to maintain the instrument to be substantially co-axial with the cannulated guide. The resilient member of the spring portion may be a spring or a solid structure having at least one cut, either of said spring or said cut adapted to impart compressibility, expandability, or both. The spring portion may be made of PEEK, nitinol, stainless steel, Radel, ABS, polycarbonate, polyethylene, PTFE, or any combination.

In yet another embodiment, the present invention includes a drill for use in soft tissue repair, the drill comprising a shaft having a distal end, a proximal end and a length therebetween, a distal drilling tip, and a bushing having a length, wherein at least a portion of the length of the bushing includes a solid portion and at least another portion of the length of the bushing includes a spring portion, said spring portion including a resilient member. The distal-most portion of the bushing may be the solid portion. Moreover, the bushing, along its length, may include more than one spring portion and more than one solid portion, each spring portion separated from one another by a solid portion. The bushing may also be cannulated such that the shaft of the drill may be positioned therethrough, and the bushing may be positioned on the shaft adjacent the distal drilling tip. While positioned on the shaft, the bushing may be rotatable, slideable, or both. The drill of this embodiment is adapted to be positioned through a cannulated guide, said cannulated guide having a length, a curved portion along at least a portion of its length, and a longitudinal axis extending therethrough, and the bushing may include an outer diameter adapted to position the shaft of the drill substantially coaxial with the longitudinal axis of the cannulated guide.

In still another embodiment, the present invention includes a method of preparing a bone hole in bone, the method including accessing the bone, determining a position for the bone hole, and preparing the bone hole using a surgical drill, the drill comprising a shaft having a distal end, a proximal end and a length therebetween, a distal drilling tip, and a bushing having a length, wherein at least a portion of the length of the bushing includes a solid portion and at least another portion of the length of the bushing includes a spring portion, said spring portion including a resilient member.

In a further embodiment, the present invention may include a cannulated guide for use in the repair of soft tissue, the guide including a proximal end, a distal end and a length therebetween, the distal end having a distal tip including an engagement surface having a generally angled face and an at least one edge engagement feature. The edge engagement feature may have a cross-sectional shape suitable for engagement with the bone. For example, the cross-sectional shape may be a "c" shape, a "u" shape, a "v" shape, or the like. The engagement feature may be positioned on the engagement surface to provide a prescribed offset from the anatomical edge. The angled face, and at least one edge engagement feature, may be dimensioned to be suitable for engaging anatomy for the repair of a hip labrum, for example. The guide, along at least a portion of its length, may include at least one curve, or alternatively, two or more curves. The distal end of the guide may further include a window through a portion of a sidewall of the guide.

In yet a further embodiment, the present invention may include a method of securing soft tissue to bone, the method including accessing the soft tissue and the bone, passing a filament through the soft tissue, preparing a bore hole in the bone, loading the filament into a filamentary fixation device, implanting the filamentary fixation device, with the filament, into the bore hole, and tensioning the filament so that the filamentary fixation device and filament are secured within the bore hole. The soft tissue to be secured may be, for example, shoulder labrum, hip labrum, rotator cuff, or the like. During the loading step, first and second ends of the filament may each pass through first and second ends of the filamentary fixation device. An inserter or like instrument may be used to implant the filamentary fixation device and filament within the bore hole. Also, following the accessing step, the remaining steps may be performed through a cannulated guide, and such guide may further include a curved portion along at least a portion of its length. Both the inserter and a drill, for preparing the bore hole, may include a flexible portion along at least a portion of the respective lengths to pass through the curved portion of the guide.

In another embodiment, the present invention may include a method for repairing a torn rotator cuff, the method including implanting a bone anchor in a medial location, underneath the rotator cuff, having a filament being associated with the bone anchor, the filament having a length and an end portion having an end, passing the end through the rotator cuff and positioning the end portion over the rotator cuff in a lateral direction, preparing a bore hole in the bone in a position lateral to the rotator cuff, loading the filament into a filamentary fixation device, implanting the filamentary fixation device, with the filament, into the lateral bore hole such that the end of the end portion is positioned outside of the bore hole, and tensioning the end of the filament so that the filamentary fixation device and filament are secured within the lateral bore hole and the rotator cuff is drawn towards the lateral bore hole.

Continuing with this embodiment, the filament may further include a second end portion and a second end, wherein the end portions of the filament extend from the bone anchor. In this configuration, the method may further include passing the ends of the filament through the rotator cuff and positioning the end portions over the rotator cuff in a lateral direction, preparing a second bore hole in the bone in a position lateral to the rotator cuff and adjacent to the first bore hole, loading the second end portion of the filament into a second filamentary fixation device, implanting the second filamentary fixation device, with the second end portion, into the second lateral bore hole such that the ends of the end portions are positioned outside of the bore holes, and tensioning the end of the second end portion so that the filamentary fixation device and second end portion are secured within the second lateral bore hole and the rotator cuff is drawn towards the second lateral bore hole. Once the ends of the filament are passed through the rotator cuff, the end portions may be tied into a knot to compress a portion of the rotator cuff between the knot and the bone anchor.

In another alternative configuration of this embodiment, where the filament again may include a second end portion and a second end, wherein the end portions of the filament extend from the bone anchor, the method may optionally include passing the ends of the filament through the rotator cuff and positioning the end portions over the rotator cuff in a lateral direction, loading the end portions of the filament into the filamentary fixation device, implanting the filamentary fixation device, with the filament, into the lateral bore hole such that the ends of the end portions are positioned outside of the bore hole, and tensioning the ends of the filament so that the filamentary fixation device and filament are secured within the lateral bore hole and the rotator cuff is drawn towards the lateral bore hole.

In yet another embodiment, the present invention may include a method of loading a filament onto a filamentary fixation device, the method including obtaining an end of the filament; engaging the end with a threading filament, wherein the threading filament is positioned within a loading device containing the filamentary fixation device, the threading filament passing through at least a portion of the filamentary fixation device; and tensioning the threading filament to pull the end of the filament into the loading device and through at least a portion of the filamentary fixation device.

The filament of this embodiment may, prior to the engaging step, be passed through a tissue, a suture anchor, or both. After the tensioning step, the method may further include disengaging the end of the filament from the threading filament. After the tensioning step, the method may also include opening the loading device and removing the filamentary fixation device and filament from the loading device. The loading device may also house an inserter instrument, such that, the step of removing the filamentary fixation device and filament from the loading device further includes securing the filamentary fixation device and filament to the inserter, and removal of the inserter, with the filamentary fixation device and filament, from the loading device.

In yet another embodiment, the present invention may include a method of loading a filament onto a filamentary fixation device, the method including obtaining first and second ends of the filament, having a length between the ends; engaging the first and second ends with first and second threading filaments, wherein the threading filaments are positioned within a loading device housing the filamentary fixation device, the threading filaments passing through at least a portion of the filamentary fixation device; and tensioning the threading filaments to pull the first and second ends of the filament into the loading device and through at least a portion of the filamentary fixation device.

The filament of this embodiment may, prior to the engaging step, be passed through a tissue, a suture anchor, or both. After the tensioning step, the method may further include disengaging the first and second ends of the filament from the first and second threading filaments. After the tensioning step, the method may also include opening the loading device and removing the filamentary fixation device and filament from the loading device. The loading device may also house an inserter instrument, such that, the step of removing the filamentary fixation device and filament from the loading device further includes securing the filamentary fixation device and filament to the inserter, and removal of the inserter, with the filamentary fixation device and filament, from the loading device.

In another embodiment, the present invention includes a system for the repair of soft tissue including at least one filament, at least one filamentary fixation device, at least one instrument for insertion of the filament and fixation device, and a surgical procedure. The surgical procedure may include instructions or protocol for using the filament, fixation device, and instrument to repair soft tissue.

In an associated embodiment, the present invention includes a method of providing instructions or information to practice any of the various methods of performing soft tissue repair described herein. For example, the method may include supplying a surgical protocol, or like document, to provide step-by-step instructions for performing any of the method embodiments of the present invention.

BRIEF DESCRIPTION OF THE DRAWINGS

FIGS. 3A illustrates one embodiment of an inserter, where a portion of a shaft of the inserter is transparent for illustrative purposes, in accordance with the present invention.

FIGS. 3B-3D illustrate various aspects of the inserter of FIG. 3A, in accordance with the present invention.

FIG. 6B illustrates a portion of the cannulated guide as transparent to show underlying details, in accordance with the present invention.

DETAILED DESCRIPTION

Figure 1A:
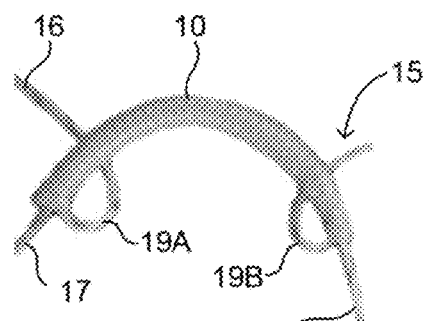
FIGS. 1A and 1B illustrate one embodiment of a filamentary fixation device in accordance with the present invention.

The disclosure herein relates to various devices and instrumentation for use with a filamentary fixation device of the present invention. More particularly, the various devices and instrumentation may be used with a filamentary fixation device for the repair of soft tissue. Such devices and instrumentation may be used in a wide array of methods, systems, kits, and like embodiments, of which various exemplary embodiments will be described in detail below. Other embodiments utilizing the various devices and instrumentation are also envisioned.

As used herein, the term "surgeon" may refer to any clinician, nurse, assistant, doctor or the like who may utilize the present invention. The terms "proximal" and "distal" are used herein relative to the surgeon, such that "proximal" means closer to the surgeon and "distal" means further from the surgeon.

The term "soft tissue" refers to any tissue such as ligaments, tendons, capsule, cartilage, meniscus, and the like. The term "bone" refers to bone or hard tissue, and includes both cortical and cancellous bone.

While the devices, instruments, kits, systems and methods of the present invention are intended for use in arthroscopic surgical applications, they may of course be used in open surgical procedures.

Generally speaking, the present invention, in one embodiment, is a system for repairing soft tissue, the system includes at least a filamentary fixation device 10, a filament 15, an inserter 20, a cannulated guide 40, and a loading device 50. The system can further include a drill 60 having a bushing 67 thereon. The system may still further include various instrumentation such as awls and trocars. Any of the inserter, drill, awl or trocar is capable of being positioned through the cannulated guide, as will be discussed in greater detail below.

Figure 1B:
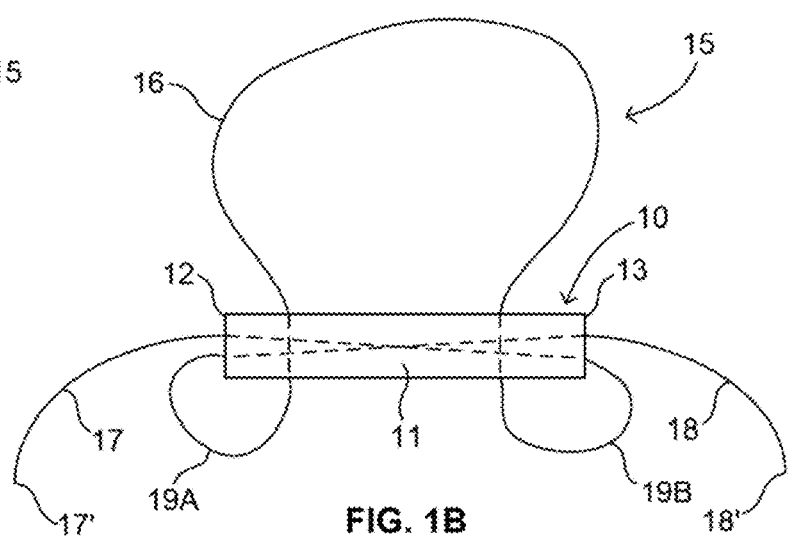
Figure 2:
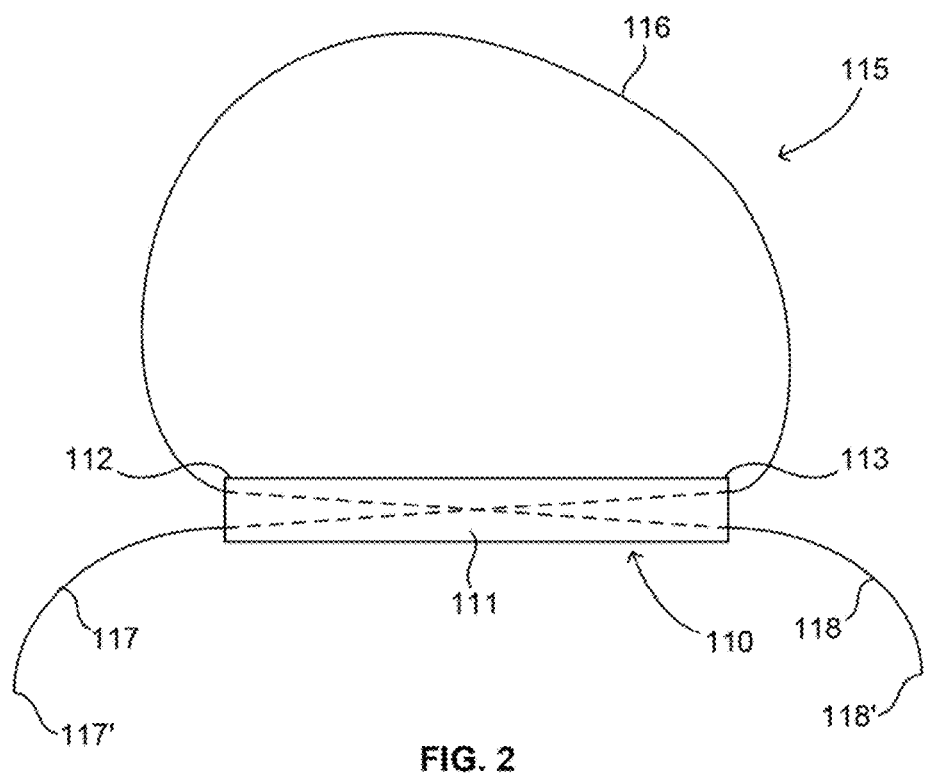
FIG. 2 illustrates another embodiment of a filamentary fixation device in accordance with the present invention.

Various embodiments of the filamentary fixation device 10, 110 of the present invention are illustrated in FIGS. 1A-2. FIGS. 1A-1B illustrate one embodiment of the filamentary fixation device 10 having a filament 15 loaded thereon. The device 10 includes a substantially tubular or cylindrical shape with a first end 12 and a second end 13, and a hollow interior 11. Alternatively, the device 10 may have a substantially flat shape. The device 10 is formed of filament material. The filament 15, also formed of filament material, includes a first end 17' and a second end 18' and a length therebetween. Once loaded (discussed below) onto the device 10, the filament 15, so configured, may include a loop portion 16, a first portion 17, and a second portion 18. The filament 15 as illustrated may further be configured to include first and second secondary loops 19a, 19b such that the filament 15, starting with loop 16, passes transversely through the device 10 and then into the ends 12, 13 of the device, forming secondary loops 19a, 19b. The first and second portions 17, 18 then extend through the interior 11 and out the opposite end 12, 13 of the device 10, from which they entered, and terminate at first and second ends 17', 18' of the filament 15. As will be discussed in more detail below, such an arrangement creates, for each filament portion 17, 18, a one-way tensioning mechanism such that the filament ends 17', 18' may be tensioned, by pulling in one direction, and such tension, once applied, will not loosen under normal operation.

FIG. 2 illustrates another embodiment of the filamentary fixation device 110 having a filament 115 loaded thereon. In this embodiment, device 110 includes a substantially tubular or cylindrical shape with a first end 112 and a second end 113, and a hollow interior 111. The device 110 is formed of filament material. Alternatively, the device 110 may have a substantially flat shape. The filament 115, also formed of filament material, includes a first end 117' and a second end 118' and a length therebetween. Once loaded (discussed below) onto the device 110, the filament, so configured, may include a loop portion 116, a first portion 117, and a second portion 118 such that the filament 15, starting with loop 16, proceeds into the ends 112, 113 of the device 110. The first and second portions 117, 118 then extend through the interior 111 and out the opposite end 112, 113 of the device 110, from which they entered, and terminate at first and second ends 117', 118'. Once again, this configuration may create a one-way tensioning mechanism as to each end portion 117, 118.

Both the device 10, 110 and filament 15, 115 are formed of flexible elongate materials may be fine or thinly spun thread, wire, fiber, or any other suitable material. For example, the material may include suture material such as polyester, UHMWPE polymer, or the like. However, the materials for either the device or the filament are not necessarily limited to a thread, suture, fiber, or wire. Additionally, the device and filament may be formed of the same material as once another or difference materials from one another. Further, the device and filament may have differing construction from one another, such as different weaving, density, or the like.

Further, the device 10 should have a diameter which is larger than that of the filament 15, such that the filament may be positioned within the hollow interior 11 of the device. Preferably, the diameters should be sufficiently sized to allow two portions of filament 15 to be positioned within the interior 11, as illustrated. While the material of the device 10 should be hollow, the material of the filament 15 may have a hollow core or a solid core, depending on the application and the strength of the material required. Alternatively, the filament 15 may be constructed of metal wire or other like material.

With respect to the embodiment of the device having a substantially flat shape, rather than positioning the filament through a hollow interior, the filament may instead pass through the device in a direction transverse to the longitudinal axis of the device. The filament may pass at least once through the device in this fashion. For example, the filament may pass through a first side of the flat-shaped device and out a second side. Then, the filament may pass through the second side, at a second location, and out the first side. This passage of the filament may be repeated as desired. Other configurations are also envisioned using such a flat-shaped device.

While FIGS. 1-2 illustrate certain embodiments of the filamentary fixation device and filament of the present invention, it is envisioned that alternative configurations of the device may also be incorporated into the various systems, methods as well as used with the various instrumentation herein. For example, alternative configurations are disclosed in U.S. application Ser. No. 13/303,849, filed Nov. 23, 2011, and U.S. Pat. Nos. 5,989,252 or 6,511,498, the entireties of which are incorporated by reference herein as if fully set forth herein. Other alternative configurations are also envisioned.

FIGS. 3A-D illustrate one embodiment of an inserter 20 of the present invention for use with a filamentary fixation device, such as device 10 of FIGS. 1A-1B, for example. The inserter 20 includes a distal portion 30 and a proximal portion including a handle 21, and a shaft extending therebetween. The shaft includes a proximal shaft 22 and a distal shaft 24, where the proximal shaft 22 has a larger diameter than the distal shaft 24, as illustrated. At the juncture of the proximal and distal shafts is a shoulder 23, or like structure, which may operate as a stop when the inserter 20 is used in conjunction with a cannulated guide 40 (discussed in greater detail below). A laser marking 81, gap in material (e.g., an incomplete cylinder of material at the proximal end), or the like, may also be positioned on the proximal shaft 22 to denote the position of the inserter 20 to the surgeon during use (e.g., when the distal portion 30 is within a surgical site in a patient). For example, as described below, the laser marking 81 may assist the surgeon in knowing where the stop 23 is positioned within the cannulated guide 40, and thus, where the distal portion 30 of the inserter 20 is relative to, for example, the bone or a prepared bore hole in the bone. Inserter 20 may be constructed of any suitable material for surgical applications including stainless steel, Nitinol, plastics or the like. Preferably, stainless steel may be used.

Figure 3C:
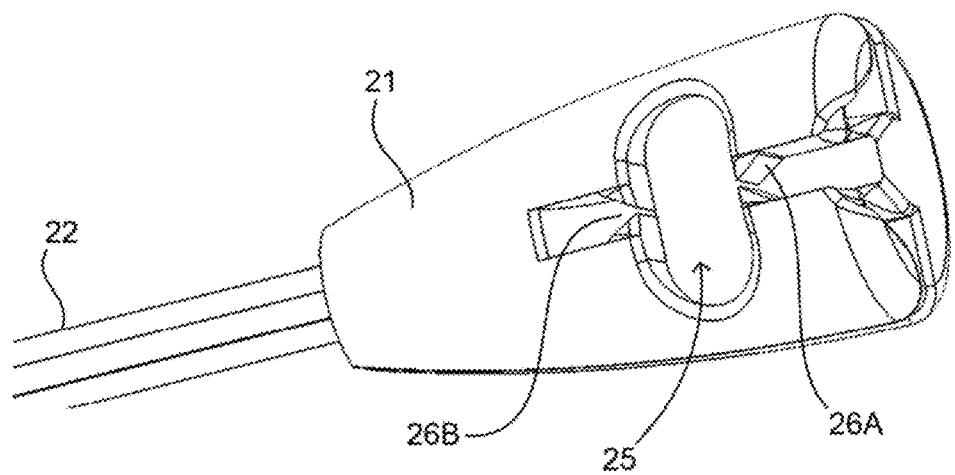
Figure 3D:
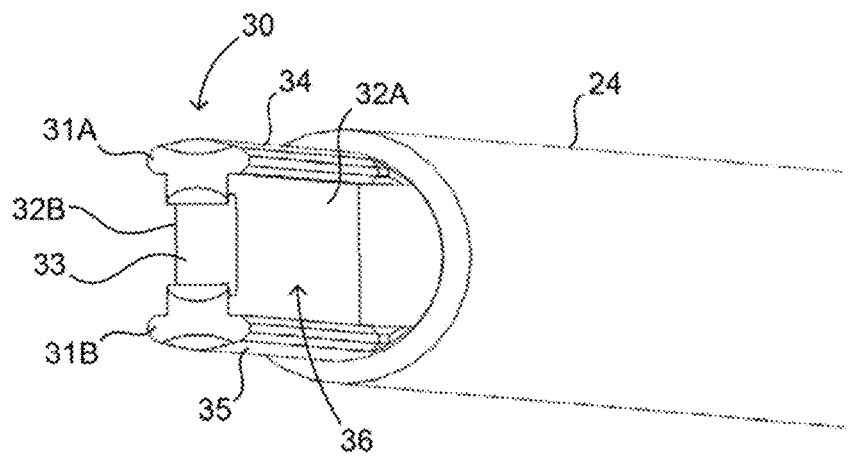
Figure 4:
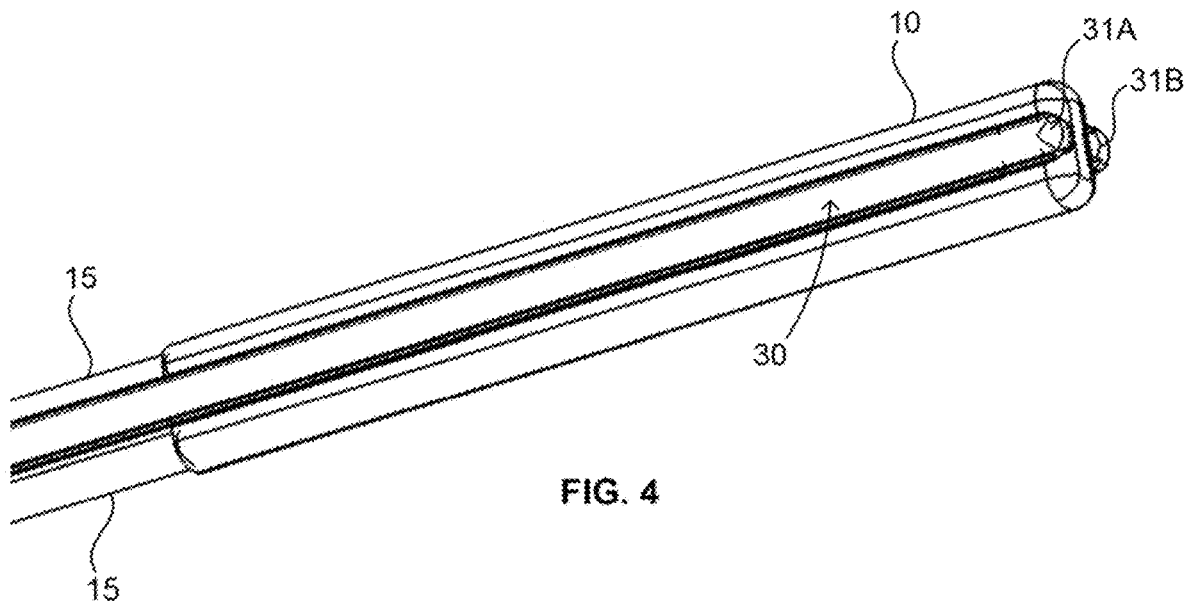
FIG. 4 illustrates the inserter of FIGS. 3A-D having a filamentary fixation device positioned thereon, in accordance with the present invention.

The distal portion 30, as seen best in FIG. 3D, may include an I-beam shape along its length which includes I-beam struts 34, 35 and a central support 36. The I-beam struts may have a substantially curved outer surface to minimize sharp corners along the distal portion 30 as well as to mimic the shape of the cannula of the cannulated guide, as discussed below. The I-beam shape provides for first and second grooves 32a, 32b defined on either side of the central support 36 by the struts 34, 35. The distal-most end of distal portion 30 includes a saddle 33 defined between I-beam projections 31a, 31b and a cut-out portion of the central support 36. The I-beam projections 31a, 31b, as illustrated, form a forked end. However, the distal-most end of the inserter may have other shapes such as a flat blade end, a flat blunt end, or the like. As illustrated in FIG. 4, the grooves 32a, 32b and saddle 33 (see FIG. 3D) are adapted to accommodate a filamentary fixation device (such as device 10 of FIGS. 1A-1B) therein, and as such the distal-most end may include any structure suitable for accommodating the filamentary fixation device. The distal portion 30 of the inserter may have a width of about 1.3 mm, measured from the outer edges of the I-beam struts 34, 35 as to the embodiment of FIG. 3D. At such a dimension, an inserter 20 constructed of stainless steel may have sufficient flexibility to pass through a curved cannulated guide (see FIG. 7A) while still having sufficient strength when, for example, the surgeon presses or uses a mallet on the inserter to implant the device 10 into a bore hole in bone.

FIG. 3C illustrates the proximal portion of the inserter 20 including handle 21. The handle includes a filament engagement structure 25 including first and second cleats 26a, 26b. For example, the engagement structure 25 may be used to secure filament 15 after it has been loaded into device 10 and the device and filament have been secured to the distal portion 30 of the inserter 20, such that the first and second portions 17, 18 of the filament 15 may be tensioned proximally, towards handle 21, and engaged within the engagement structure 25.

Figure 5A:
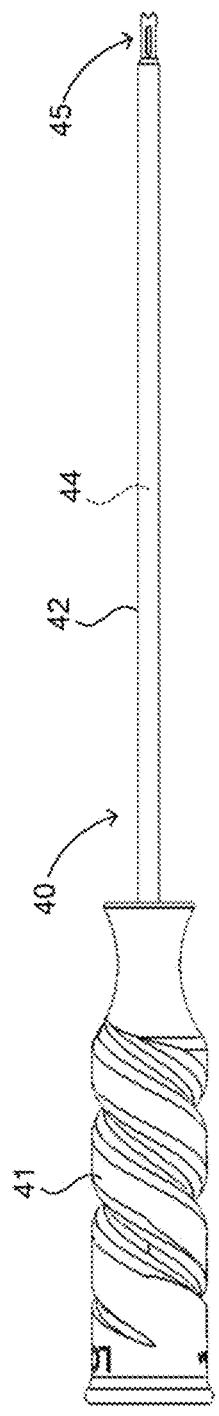
FIGS. 5A-5C illustrate various aspects of one embodiment of a cannulated guide in accordance with the present invention.
Figure 5B:
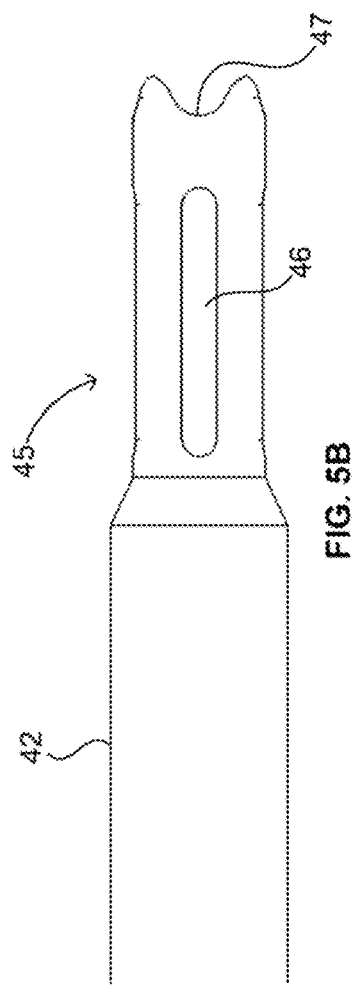
Figure 5C:
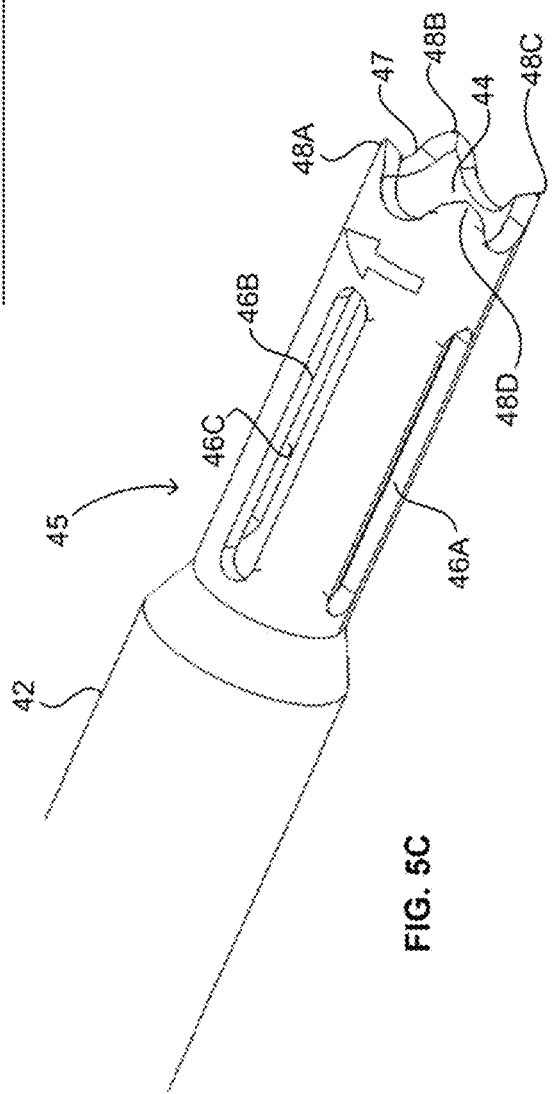

FIGS. 5A-5C illustrate one embodiment of the cannulated guide 40 having a proximal end including handle 41 and a distal end including distal tip 45, and a shaft 42 positioned between handle 41 and distal tip 45. At least a portion of the length of the cannulated guide is cannulated. Preferably, and as illustrated, the cannulated guide may have a cannulation 44 through the entire length of the guide 40, extending from the proximal-most end of the handle 41, through the handle and shaft 42, and out the distal-most end of the distal tip 45. This cannulation 44 of the guide may be adapted to accommodate the inserter 20 and/or the drill 60 (described below). The overall length of the guide may be dependent on the anticipated surgical procedure, anticipated directional approach by the surgeon, as well as other factors. For example, in a preferred embodiment, a possible guide length for use in a shoulder application, such as for the repair of a rotator cuff, may be about 5.2 in., while a possible guide length for use in an instability application, such as for the repair of a hip or shoulder labrum, may be about 7.1 in. Of course, these dimensions are only exemplary and other lengths are envisioned.

Figure 8A:
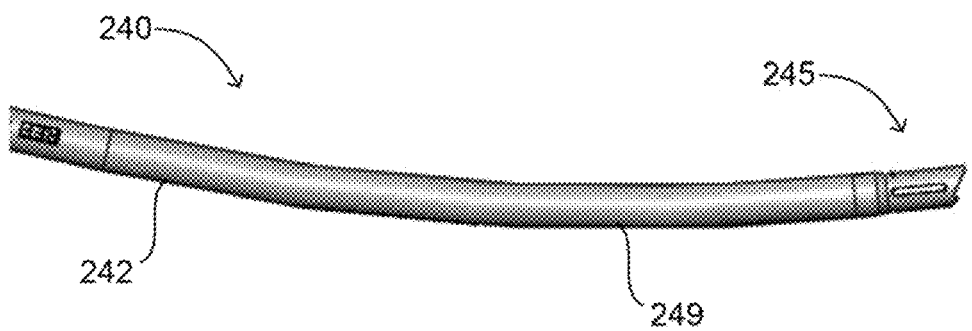
FIGS. 8A-8C illustrate another embodiment of the cannulated guide in accordance with the present invention.
Figure 8B:
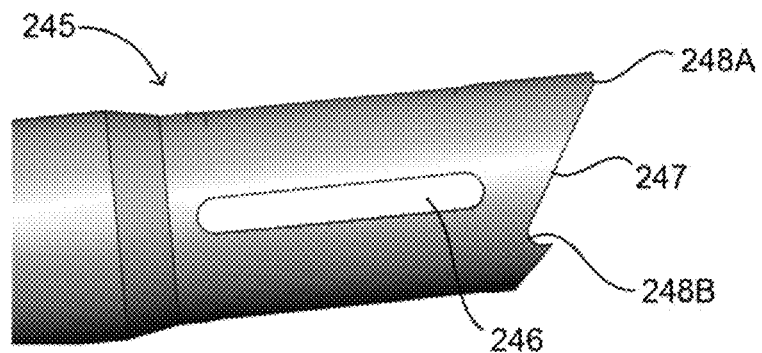
Figure 8C:
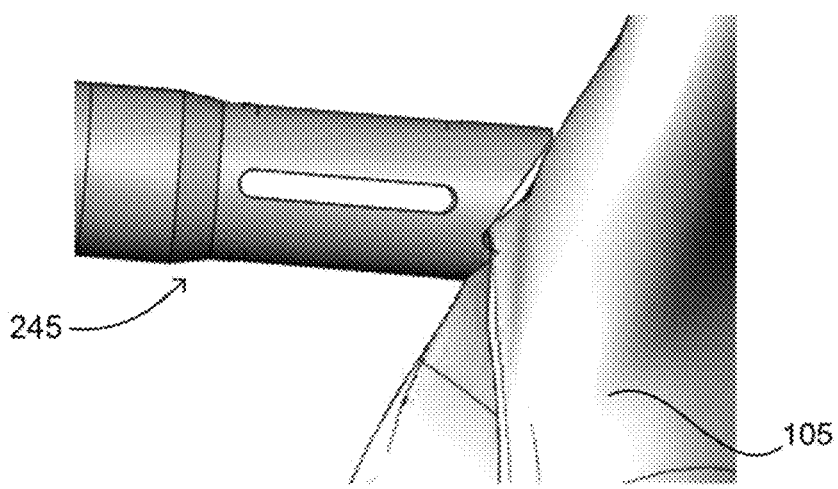

With reference to FIGS. 5B and 5C, the distal tip 45, extending from shaft 42, includes an at least one window 46 and an engagement surface 47. The distal tip may include more than one window 46a, 46b, 46c (see FIG. 5C) to provide viewing capability, for the surgeon, of the cannulation 44 from a variety of directions. The engagement surface 47 is adapted to engage a portion of the anatomy of the patient, and specifically, to engage the surface of the bone, or the like. As illustrated, the surface 47 may include a "crown" shape including four prongs 48a, 48b, 48c, 48d, wherein the prongs may engage bone to maintain a stable connection between the bone and the guide 40. Other engagement surface structures are also envisioned which may be useful for particular angles of approach to certain anatomy, as well as the bone surface or other anatomical shape to which the distal tip of the guide must engage. For example, FIGS. 8A-8C illustrate an alternative distal tip 245 having an engagement surface 247 including an angled face extending to a distal-most end 248a and including an at least one edge engagement feature 248b which may be positioned on the engagement surface 247. This embodiment will be discussed further below.

Continuing from the embodiment of FIGS. 5A-5C, FIGS. 6A and 6B illustrate additional detail of one embodiment of the proximal portion of the cannulated guide 40, including handle 41. The cannulation 44 may pass completely through the length of the guide, as shown, such that the cannulation extends through the handle 41 and out the proximal-most end 91 of the guide and handle. The cannulation may include a shoulder or stop 43 which may interact with the stop 23 of the inserter 20 (or a similar structure on the drill 60, discussed below) to limit distal movement of the inserter through the cannulated guide. In one embodiment, the laser mark 81 (or gap of material, or the like) of the inserter 20 may be positioned on the shaft 22 such that, upon contact of the stop 23 and stop 43, the laser mark 81 aligns with the proximal-most end 91 of the handle 41. Furthermore, as discussed in greater detail below, the proximal-most end 91 of the handle 41 may include a color marking thereon to designate, to the surgeon, that the cannulation 44 has a specific, known, diameter. This may be particularly beneficial if the surgeon has a plurality of guides 40 and inserters 20 and/or drills 60, for example as in a kit of such instruments, such that the surgeon may use such color coding to use the proper guide and inserter/drill combination (as mentioned below, the inserters and drills may also have such color coding, for example on a proximal portion, such as handle 21 of the inserter 20 or on bushing 67 of the drill).

Figure 7A:
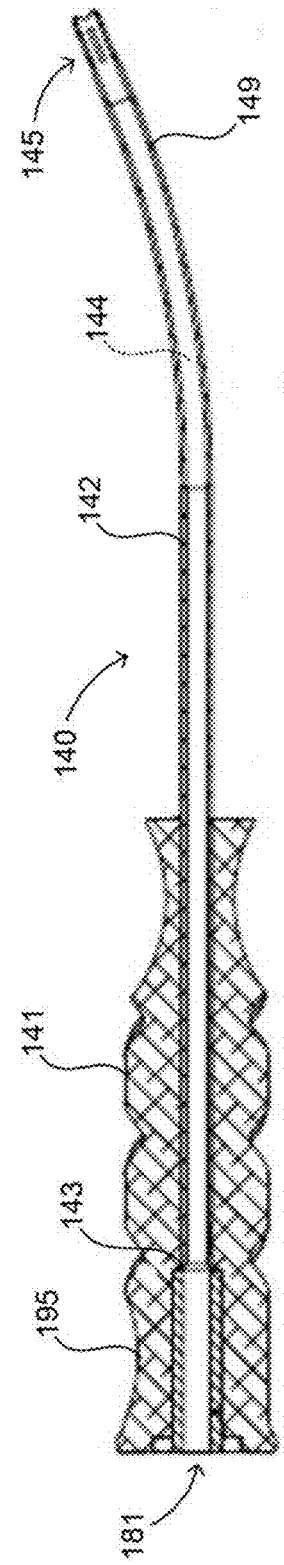
FIG. 7A illustrates another embodiment of a cannulated guide in accordance with the present invention.
Figure 7B:
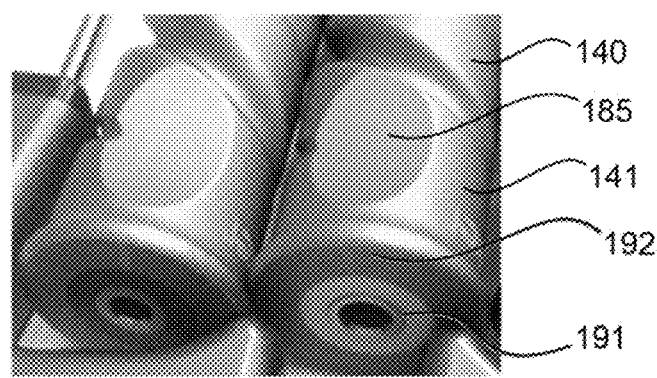
FIG. 7B illustrates details of a portion of the cannulated guide of FIG. 7A in accordance with the present invention.

FIGS. 7A and 7B illustrate another embodiment of a cannulated guide 140 including a proximal portion having a handle 141 and a distal portion including a distal tip 145, and a shaft 142 positioned between handle 141 and distal tip 145. In this embodiment, contrary to guide 40, the shaft 142 may include a curve 149 along at least a portion of its length, as illustrated in FIG. 7A. The curve may have an angle of curvature suitable for a particular procedure, approach angle to an anatomical location, a specific anatomy, or the like. For example, the guide 141 may have a curve 149 having an angle of curvature greater than 0 degrees up to and including about 180 degrees. Preferably, the curve may have an angle of curvature of, for example about 12 degrees or about 25 degrees. Additional examples of curved guides are disclosed in co-pending applications, assigned to the same assignee as the present application, including U.S. application Ser. No. 13/368,730, and U.S. Publication Nos. 2011/0015674, 2011/0015675 and 2011/0208194, the entireties of which are hereby incorporated by reference herein as if fully set forth herein. Of course, cannulated guides having multiple curved portions, with similar or different angles of curvature, are also within the scope of this invention.

It should be noted that any of the disclosed cannulated guides may also be in the form of a slotted guide (not shown), wherein the slotted guide does not include a guide having a complete, uninterrupted, cylindrical shape, but instead includes an incomplete cylindrical shape. Thus, such a slotted guide would include a channel through the interior of the slotted shape rather than a cannulation.

Continuing with this embodiment, FIGS. 7A and 7B may include various structures adapted to designate to the surgeon in which direction the curve 149 is positioned. Such structures may be particularly useful when, for example, the guide is positioned within the patient during arthroscopic surgery. First, the handle 141 may include an indent 195 positioned on the handle relative to the curve 149. As in FIG. 7A, the indent 195 may be positioned on the handle 141 on substantially the same side as the curve 149 is angled towards. In this example, the curve 149 is angled in an upward direction, and the indent 195 is also positioned in an upward direction, on the upward portion of the handle 141. Of course, the relative positioning can be altered as desired. Moreover, the indent 195 as illustrated is shaped such that the surgeon can position a thumb therein, though other shapes may also be incorporated suitable for positioning a finger, a portion of the palm, or the like therein. Further, the handle may include a plurality of indents, any of which may be used to designate the curve. Second, as illustrated in FIG. 7B, the proximal-most portion 191 of the handle 141 may include a laser mark or other marking 192 which may also be used by the surgeon to orientate the curve 149 when not being able to see the curve, e.g., when the distal portion of the guide is positioned within the patient.

In another embodiment (not illustrated), the guide of the present invention may include more than one curve along its length. For example, the guide may have a first curve, as discussed above, towards the proximal end of the guide. The guide may also have a second curve, proximal to the first curve. These curves may have trajectories, angles, and lengths different from one another or the same as one another, such that a multitude of various guides may be created. Such dual-curve guides may be particularly useful for surgical procedures with a difficult angle or direction of entry into the anatomy, such as a hip labrum repair or the like.

A further embodiment of a cannulated guide is illustrated in FIGS. 8A-8C, which illustrates a cannulated guide 240 including a shaft 242 and a distal tip 245 having an engagement surface 247 which may be used, for example, in procedures for repairing a hip labrum tissue. The surface 247, rather than a "crown" shape, instead includes an angled face extending to a distal-most end 248a of the angled face. As illustrated for example in FIG. 8B, the angled face is designed to have an angle which is not perpendicular, relative to a longitudinal axis of the cannulated guide. The angled face also includes an at least one edge engagement feature 248b which may be positioned on the engagement surface to provide a prescribed offset from an anatomical edge or other feature of the bone 105. As illustrated, the edge engagement feature 248b is positioned on the engagement surface a distance away from the distal-most end 248a. Such a configuration as illustrated may be beneficial for use in repairing a hip labrum tissue, for example, because of the angle of approach to the anatomy the surgeon must use, as well as the shape of the bone 105 to which the labrum tissue will be attached. This type of distal tip 245 may provide for sufficient engagement of the distal tip to the anatomy despite the angled approach to the anatomy. FIG. 8C illustrates such an engagement with the anatomy of the acetabulum 105 of the hip, for example.

The engagement feature 248b may have a cross-sectional shape suitable for engagement with the bone. For example, the cross-sectional shape may be a "c" shape, a "u" shape, a "v" shape, or the like. For example, as illustrated in FIG. 8B, the engagement feature 248b has a "c" cross-sectional shape. The distal tip 245 may also include a window 246 through a portion of the sidewall of the guide. The guide, as illustrated in FIG. 8A may include at least one curve 249, or alternatively, two or more curves, along at least a portion of its length. As with other embodiments, if two or more curves are present along its length, the various curves may have trajectories, angles, and lengths different from one another or the same as one another. The curve or curves, angle of the engagement surface 247, positioning and number of at least one edge engagement feature 248b, and the like may be designed and manufactured for optimal ease of use in navigating the surrounding anatomy of the hip, for example, and for proper engagement to the specific portion of bone 105, such as the acetabulum 105. While this embodiment is directed to an exemplary use in reattaching a hip labrum to the acetabulum, this guide may be used in other joints and applications where an angled engagement surface, and an at least one curve, would be useful or preferred.

Figure 9A:
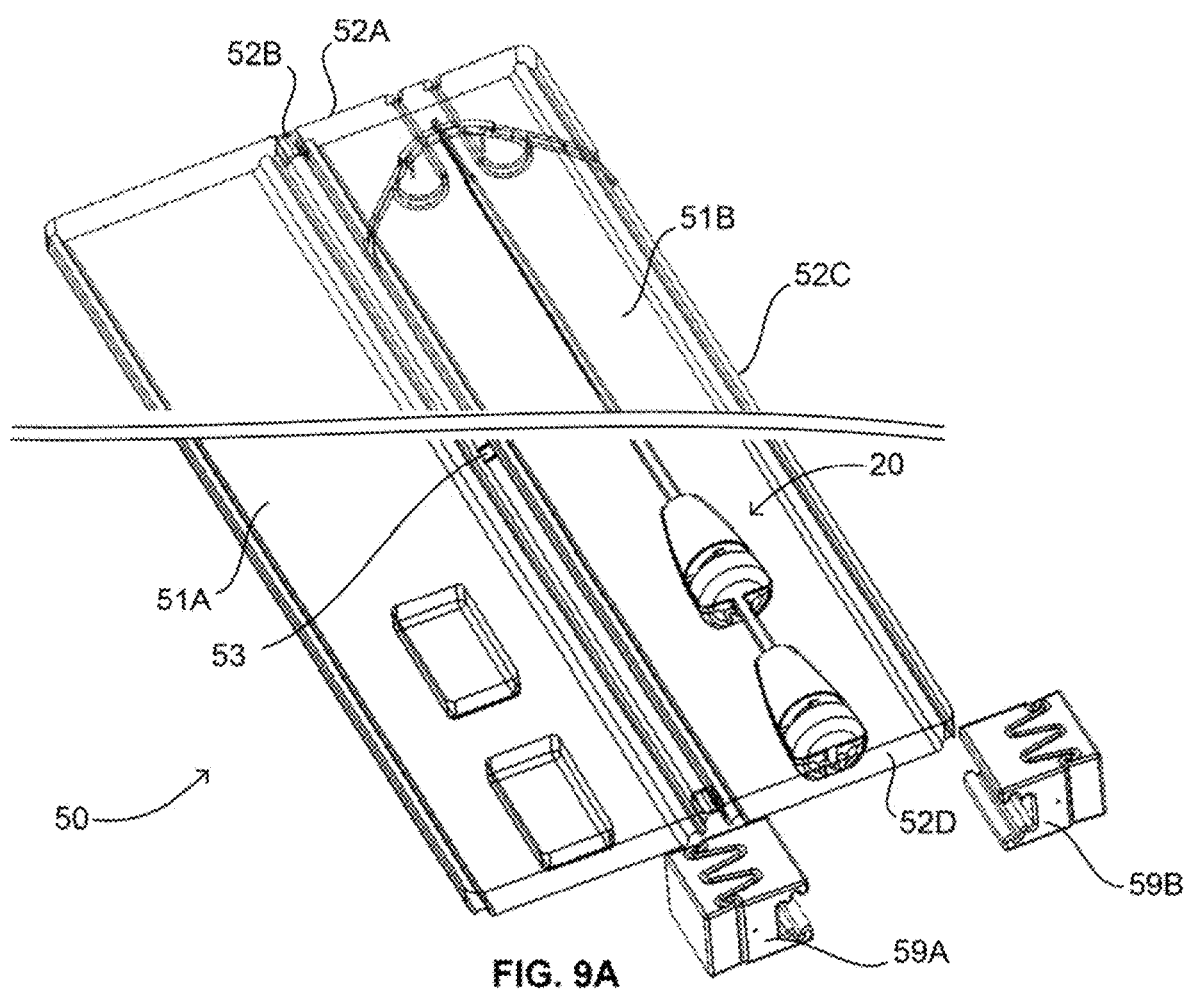
FIGS. 9A-9C illustrate one embodiment of a loading device in accordance with the present invention.
Figure 9B:
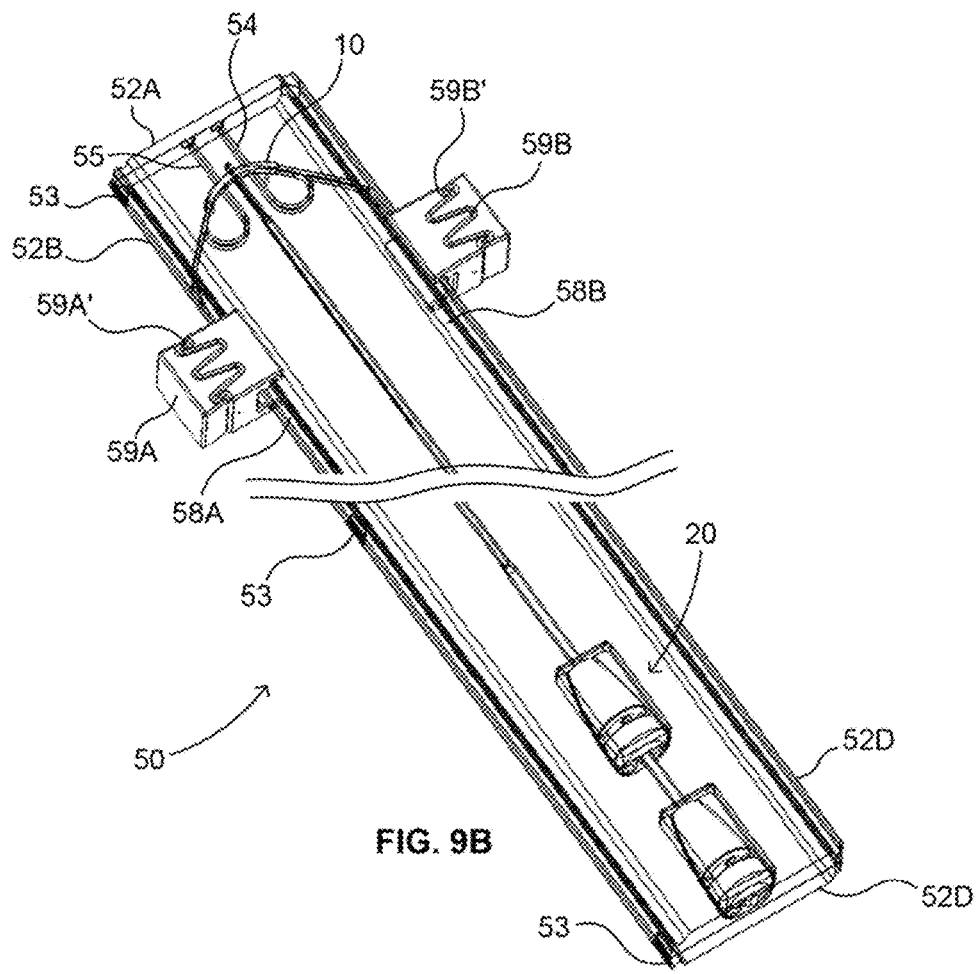
Figure 9C:
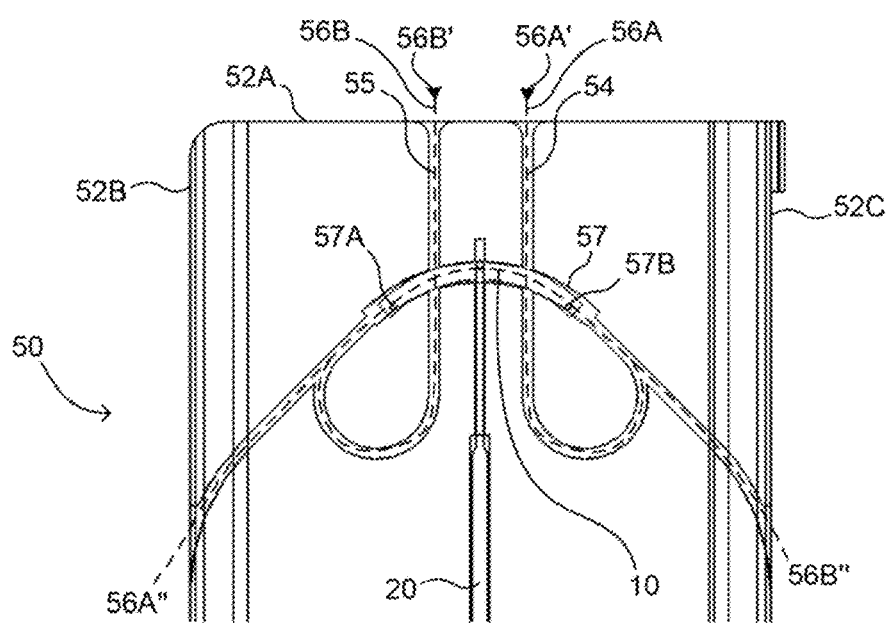

FIGS. 9A-C illustrate one embodiment of the loading device 50 of the present invention. The loading device includes a casing including an upper casing 51a and a lower casing 51b in a hinged relationship along a side of the device 50, such as hinges 53. The loading device 50, as in FIG. 9B, includes a first side 52*a*, a second side 52*b*, a third side 52*c*, and a fourth side 52*d*. In the illustration, the hinges 53 are positioned along the second side 52*b* of the device 50, though the hinges, or other like connection structure, may be positioned along other sides, as desired. Alternatively, upper and lower casings 51*a*, 51*b*, may be completely separate, such that they may be pulled completely apart from one another. As illustrated, the upper and lower casings 51*a*, 51*b* may, in a closed position, house at least a portion of the filamentary fixation device 10 and at least a portion of inserter 20 (FIGS. 9A and 9B illustrate two different sized inserters for illustrative purposes, preferably, only a single inserter would be positioned within loading device 50). Both upper and lower casings may be constructed of plastic or like material and may further be transparent to allow viewing through the casing and to the device 10 and inserter 20, when the casing is in the closed position (FIG. 9B). Preferably, the casing may be constructed of PMMA, specifically Plexiglas®, PETG, or the like. As in FIG. 9C, the upper and lower casings also define a first channel 54 extending from the first side 52*a* to the second side 52*b*. The upper and lower casings may further define a second channel 55 extending from the first side 52*a* to the third side 52*c*. Both the first and second channels may have a route within the casing, examples of such routes are circuitous or tortuous routes as illustrated in detail in FIG. 9C.

Continuing this embodiment with reference to FIG. 9C, the first and second channels 54, 55 may overlap with one another along a portion of their route, such as at location 57. Location 57 may further be adapted to maintain device 10 therein, such that the device 10 is positioned along the route of both channels 54, 55. At least one pin 57*a*, 57*b* may also be positioned within at least one of the channels, preferably within location 57, where the pin or pins 57*a*, 57*b* may assist in maintaining the device 10 within location 57 by, for example, puncturing through a portion of device 10 to secure the device in a desired location. Within first and second channels 54, 55 may be positioned first and second threading filaments 56*a*, 56*b*, respectively, constructed of wire, suture, or the like. The threading filament 56*a* may include a filament connector 56*a*' on a portion of the threading filament 56*a* adjacent the first side 52*a*, and threading filament 56*b* may include a filament connector 56*b*' on a portion of the threading filament 56*b* also adjacent the first side 52*a*. As will be explained in detail below, the threading filaments 56*a*, 56*b* may be used to thread the filament 15, which may already be secured to tissue, a suture anchor, or the like, through the filamentary fixation device 10. Filament connectors 56*a*', 56*b*' may be used to engage the filament ends 17', 18'.

Opposite ends 56*a*", 56*b*" of the threading filaments 56*a*, 56*b* may extend from the opposite ends of the channels 54, 55 and out the second and third sides 52*b*, 52*c*, respectively, and may be accessible to the surgeon, such that the surgeon may, for example, tension these opposite ends to pull filament connectors 56*a*', 56*b*' (and filament ends 17', 18') towards channels 54, 55, respectively. Preferably, and as illustrated in FIG. 9B, the loading device 50 may further include loading actuators 59*a*, 59*b* positioned on the loading device, preferably adjacent the locations where opposite ends 56*a*", 56*b*" exit from channels 54, 55. The loading actuators 59*a*, 59*b* may be slideable, or otherwise actuable, relative to the casing 51*a*, 51*b*. In this embodiment, the loading actuators may slide along sliding grooves 58*a*, 58*b* on upper and lower casings 51*a*, 51*b*. The loading actuators may also include a filament lock 59*a*'. 59*b*' through which, for example, the threading filaments 56*a*, 56*b* may be positioned. Thus, as the surgeon actuates the loading actuators, by moving them rearwards along the casing, towards side 52*d* (from the position shown in FIG. 9B to the position shown in FIG. 9A), the threading filament may be tensioned such that the filament connectors 56*a*', 56*b*' (and filament ends 17', 18') move towards, and into, channels 54, 55, respectively. Additionally, the loading actuators may also hold the upper and lower casings in a folded relationship (FIG. 9B) such that, once they have been slid rearwards, and off of the sliding grooves 58*a*, 58*b*, the upper and lower casings may be moved to an open relationship (FIG. 9A).

Figure 10A:
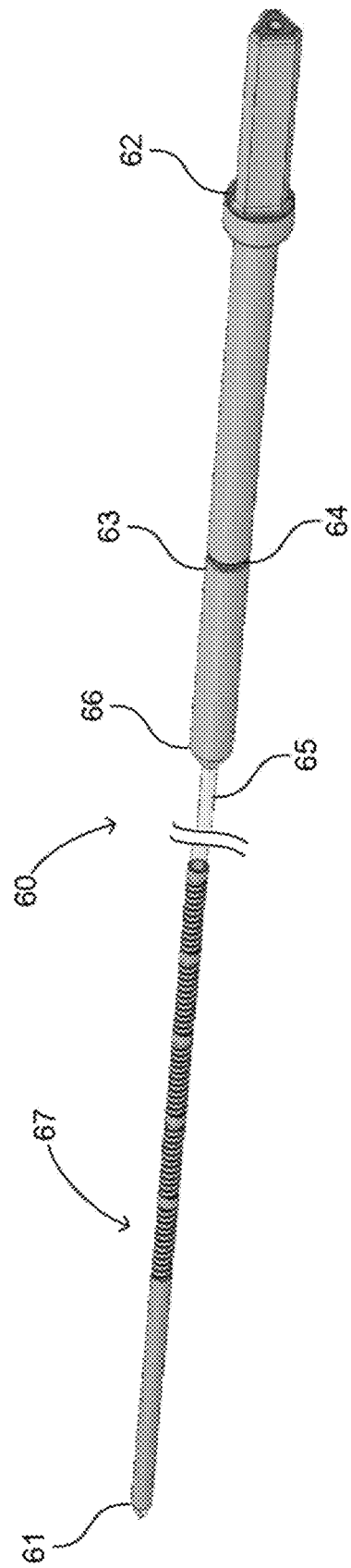
FIGS. 10A-10B illustrate one embodiment of a drill, including a bushing positioned thereon in accordance with the present invention.
Figure 10B:
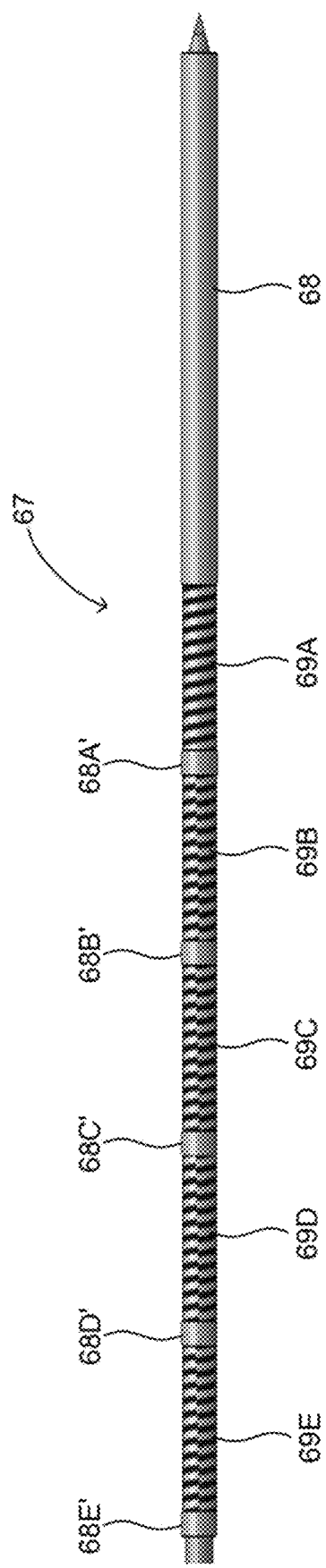

Illustrated in FIGS. 10A and 10B is one embodiment of a drill 60 of the present invention, including a distal drill tip 61, a proximal portion including a chuck 62 for connection to a power drill (not shown) and a shaft spanning a length between the distal tip and the chuck. The drill tip 61 may be any drill tip suitable for penetrating bone and/or soft tissue. The chuck 62 may be any suitable structure for engagement with a power drill. The shaft includes a proximal portion 63 and a distal portion 65, and as illustrated, the distal portion 65 may have a smaller diameter than the proximal portion 63. Between the proximal and distal portions of the shaft may be a shoulder or stop 66, which may be, for example, a shoulder for engagement with a guide, such as cannulated guide 40. Stop 66 is similar to stop 23 of inserter 20 such that either may be engageable with the same cannulated guide 40 and stop 43. An at least one laser mark 64, similar to laser mark 81 on the inserter 20, may also be positioned on the shaft, preferably, and as illustrated, on the proximal portion 63 of the shaft. Alternatively, the shaft may have a gap of material, or the like. At least a portion of the shaft, such as for example at least a portion of the distal portion 65 of the shaft, may be flexible such that it may pass through a curved cannulated guide (see FIG. 7A). The shaft may be constructed of any material which is strong enough to withstand drilling forces when preparing a bore hole in bone, but flexible to pass through a curved cannulated guide. For example, stainless steel, Nitinol, or the like may be suitable, and more specifically, a Nitinol K-wire, may be used for at least the distal portion 65 of the shaft. The Nitinol K-wire may, for example, maintain sufficient flexibility to pass through the curved cannulated guide up to a temperature of about 40 to about 60 degrees Celsius.

Drill 60 may further include a bushing 67, the bushing 67 includes a solid portion 68 and an at least one spring portion 69*a* along its length. The spring portion includes a resilient member, such that the spring portion can be compressed, expanded, or both. Bushing 67 may be positioned towards the distal end of the drill, on the distal portion 65 of the shaft. Upon activation of the drill, the bushing may either rotate with the drill (and therefore, be at least in part secured to the drill), or the drill may rotate within the bushing. The bushing may be slideable along at least a portion of the length of the distal shaft 65 and may further be compressible along the spring portion 69*a* or portions 69*a*, 69*b*, 69*c*, 69*d*, 69*e* as illustrated. The bushing may generally be flexible or elastic as well, to fit through a cannulated guide having a curve (see FIG. 7A). Suitable materials for use in the bushing may include stainless steel, Nitinol, PEEK, Radel, ABS, Polycarbonate, Polyethylene, PTFE or the like. Such polymer materials for the bushing may reduce or eliminate metallic debris created while drilling, which can be an issue especially when drilling through a curved guide as in the present invention. The spring portion 69*a*, or portions 69*a*, 69*b*, 69*c*, 6*d*, 69*e*, includes a resilient member and may be constructed of spring-like material which is then secured (e.g., welded, adhered, or the like) to the solid portion 68 as well as spacer portions 68a', 68b', 68c', 68d', 68e'. In one preferred example, illustrated in FIGS. 10A-10B, the solid portion and spacer portions may be constructed of PEEK while the spring portions, illustrated as having a spring structure, may be constructed of stainless steel. Such materials themselves may also impart flexible, expandable, compressible, and the like characteristics which can be beneficial for the operation of the bushing, as explained in certain of the alternative embodiments below.

Bushing 67 may, along at least a portion of its length, have an inner diameter sufficient to impart a press-fit on the shaft of the drill. For example, a proximal portion of the bushing may have such a smaller diameter to minimize proximal movement of the entire bushing. Instead, as the drill is pressed distally, and a distal portion of bushing contacts one or both of the bone surface or the distal portion of the cannulated guide, the spring portion 69a compresses such that the distal portion of the bushing compresses towards the proximal portion of the bushing. In one example, at a drill depth of about 20 mm, which is the preferred maximum depth of the bore hole, the springs supply an elastic force of about 0.5-10 lbs, more specifically about 1-4 lbs. Subsequently, once the bore hole is prepared, and the distal pressing (by the surgeon) is eased, the spring portion 69a expands such that the distal portion of the bushing moves closer to the distal tip 61 of drill 60 as the drill is removed from the bone, such that the bushing returns to its original position. While the spring portion does not in this embodiment force the drill to withdraw from the bone, the spring portion does allow the bushing to return to its original position upon removal of the drill from the bone. It should be noted that such compression of the bushing may also occur, for example, as the drill and bushing moves through a curved cannulated guide 140, in that as the bushing and drill move through the curve 149, the bushing may compress to allow the distal tip 61 room to navigate the curve. Once the distal tip 61 and at least a portion of the bushing 67 is through the curve, the spring portion 69a may decompress such that the distal portion of the bushing moves towards the distal tip 61 and to its original position.

The bushing 67 may maintain the drill 60 in a central location within the cannulated guide, e.g., substantially co-axial to the longitudinal centerline, or axis, of the guide 40. This may be particularly important when using a curved guide (as in FIG. 7A) because the curve of the guide, and the elastic properties of the drill shaft, may cause the drill to move off-center from the longitudinal axis of the guide upon exiting the guide such that the drill abuts one side of the guide. The bushing may minimize this movement, such that the drill remains substantially in the center of the guide, and along the longitudinal axis of the guide, even through the curve and after the curve, which provides for increased accuracy of placement of the bore hole by the drill tip 61.

The bushing 67 may also assist the surgeon in providing a "shock absorbing" or dampening system to the drill, particularly when the drill tip 61, for example, progresses through the cortical layer of bone and into the softer cancellous layer. The spring characteristics of the bushing 67 provides for a smoother transition when passing into the cancellous by absorbing some of the forces applied on the drill tip through pressure applied by the surgeon. Furthermore, where multiple spring portions 69a, 69b, 69c, 69d, 69e are present on the bushing, the various spring portions may have various spring constants such that the surgeon may obtain feedback through the varying spring tension and the depth of the bore hole being formed. For example, as the surgeon forms the bore hole, and as the bore hole trends deeper into the bone, each spring portion, each having increased stiffness, may compress sequentially. Thus, it becomes more difficult to compress the bushing the deeper the hole is drilled into the bone (and the further the bushing is compressed). Therefore, as the difficulty increases, the surgeon knows the intended depth is being achieved. Of course, the stop 66 may still be present to ensure that the surgeon does not drill the bore hole too deeply, and thus the increasing difficulty associated with the compressing spring provide the surgeon a warning that the stop 66 is approaching.

In an alternative configuration, the bushing may also serve to assist in retracting the drill tip 61 upon completion of the bore hole. Generally speaking, in this variation, when the surgeon completes the bore hole, and releases the downward pressure applied on the drill, the spring characteristics of the bushing may assist in retracting the drill tip proximally back towards the cannulated guide. In applying such "spring" forces, the distal-most end of the bushing may engage one or both of the bone or tissue surface or the distal end of the guide, such that the spring portions compress between the force applied by the surgeon and the abutment of the bone surface and/or a surface of the guide (for example, an indented shoulder or the like (not shown)). In order for the spring to assist in retracting the drill from the bone, a much higher spring force would likely be needed, likely about 10 lbs.

Further, again with relation to the cannulated guide 40, the solid portion 68, situated at the distal portion of the bushing 67, may prevent the spring portions from contacting the end of the cannulated guide, or other structure, which could potentially catch on the distal end of the guide, which is particularly possible in the event the drill and bushing are inserted through the guide when the guide is not positioned against a hard surface, such as bone. In order to minimize or prevent such an occurrence, the solid portion 68 is at least about 20 mm, and preferably about 25 mm This dimension, while not particularly limited when using a straight guide 40, this dimension of the solid portion may be limited when used with a curved cannulated guide 140 as it may be too difficult to move a larger solid portion 68 through the curve 149.

It should be noted that such bushings may also be used in conjunction with the inserter 20, which may provide for increased precision in implantation and insertion of the device 10 into a bore hole, particularly if a curved cannulated guide 140 is used. Alternatively, it may be desirable to use a bushing on the inserter if a larger, "universal," guide is used. In such a configuration, a bushing may be desirable for compatibility of the smaller implant and inserter (or drill) with the larger guide.

Figure 11A:
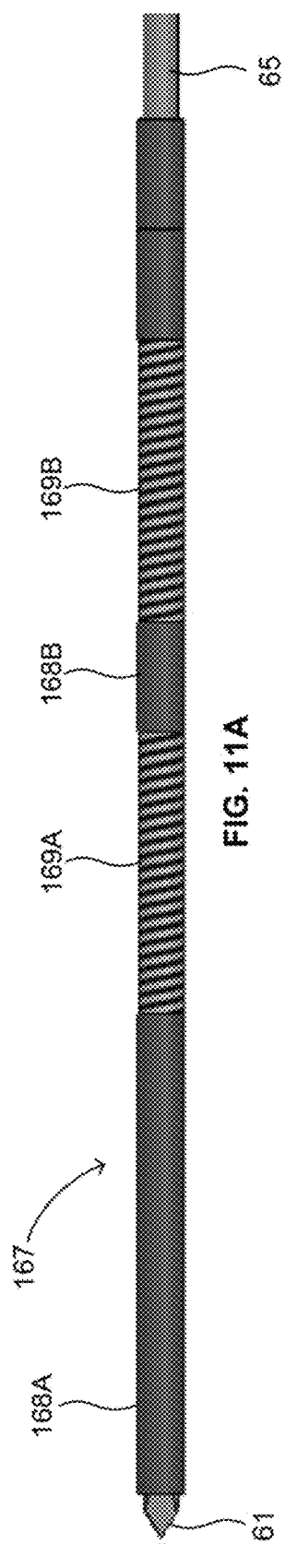
FIGS. 11A-11C illustrate various alternative embodiments of the bushing in accordance with the present invention.
Figure 11B:
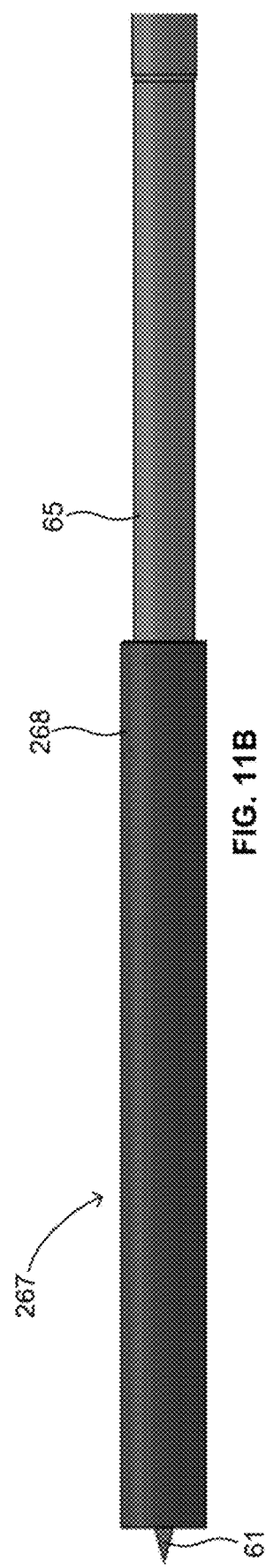
Figure 11C:
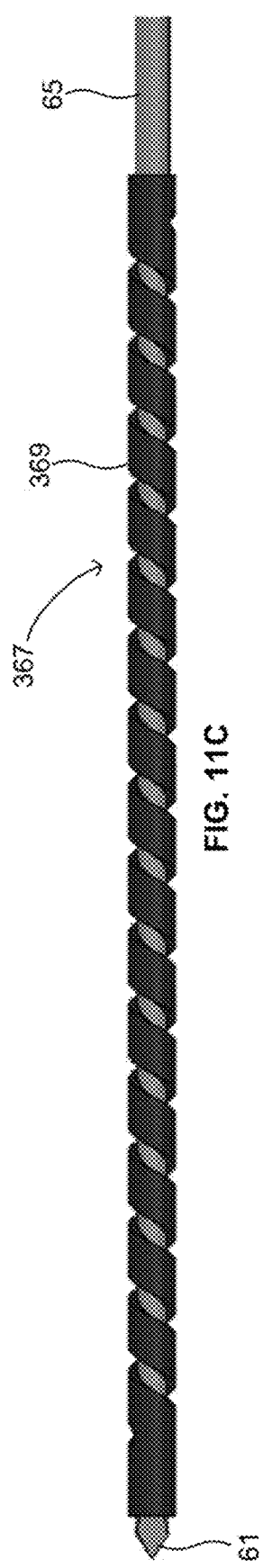

Alternative embodiments of the bushing are illustrated in FIGS. 11A-C as bushing 167, 267, 367 positioned on the distal portion 65 of the shaft of drill 60. Bushing 167 is similar to the bushing 67, though bushing 167 may include solid portion 168a as well as an at least second solid portion 168b positioned between spring portions 169a, 169b. In this embodiment of FIG. 11A, where multiple springs are utilized in the bushing, it may be beneficial to separate them by solid portions 168b to reduce metallic debris during drilling and to reduce the likelihood of the spring ends tangling in each other. Solid portions 168b may be constructed of the various polymers discussed above, though other materials such as stainless steel may be used, particularly in applications where the creation of metallic debris is less of a concern (e.g., when a guide having a mild curve, or no curve, is used).

As illustrated in FIG. 11B, bushing 267 may include only a solid portion 268 such that it does not include a spring portion along its length. Such a configuration may be sufficient to maintain the drill in a central location within the cannulated guide. Additionally, such a bushing may not have the above-mentioned spring characteristics, such that the bushing may act as an additional "hard stop" against one of the bone surface or a surface of the cannulated guide 40. Alternatively, bushing 267 may have a sufficient inner diameter such that the bushing may travel along the shaft a sufficient distance such that the bushing does not form a hard stop, but instead merely ensures that the drill remains in a central location within the guide. In both instances, the bushing may have to be manually retracted, by the surgeon, to its original starting position to create the desired "hole centering" in subsequent drill holes. Bushing 267 may be constructed of stainless steel, PEEK, or the like.

Bushing 367 is another alternative embodiment where substantially the entirety of the bushing is a spring portion 369, which operates as described above with reference to bushing 67. Bushing 367 may be constructed of, for example PEEK or Nitinol, or like material capable of providing the aforementioned spring characteristics. The bushing 367 may be manufactured from a solid piece of material and include an at least one cut, where the cut imparts the spring characteristics (resiliency such as compressibility, expandability, both, or the like). For example, the bushing 367 may be manufactured from a solid piece of material, such as PEEK, and subsequently spiral cut or molded to form the illustrated shape. Thus, in this embodiment, the entirety of the bushing 367 itself operates as the spring.

Typically, when used through a straight cannulated guide 40, for example, a drill having a small diameter may be used, such that the drill may have a diameter sufficient to form a bore hole of about 1.4 mm up to about 1.9 mm However, if a curved cannulated guide 140 is used, a slightly larger drill 60 should be used to create a bore hole of about 2.3 mm The larger dimension of the bore hole may provide easier insertion of the filamentary fixation device 10 through the curved guide and into the bore hole.

The present invention may also include various systems and kits based on the various instruments and devices discussed above. While it is envisioned that these various devices and instruments may be utilized, packaged, sold, or designed in any number of systems and kits, a few representative embodiments will be discussed in detail below.

In one embodiment, the present invention includes a system for the repair of soft tissue, the system including at least one instrument adapted to implant a filamentary fixation device into bone, and the filamentary fixation device 10. The system may further include at least one filament adapted to cooperate with the fixation device. The at least one instrument may be any or all of the above-discussed instruments used in implanting the fixation device 10.

In another embodiment, the present invention may include a system including at least one instrument for implantation of a filamentary fixation device, such as a cannulated guide 40 and an inserter 20. The system may further include a drill 60. The cannulated guide 40 includes, at its proximal-most end 91 of the handle 41, a color marking which may designate to a surgeon that the cannulation is sized to fit an inserter, or drill, having a certain dimension. As discussed throughout, the present invention includes two exemplary sizes of about 2.3 mm and about 1.4 mm Thus, the color marking of these two various sizes would be different such that, for example, the 2.3 mm cannulated guide 40 includes a black color marking, while the 1.4 mm guide includes a tan color marking. Of course, other color pairs easily discernible by the surgeon may be used. The inserter 20 of the matching dimension may also include the same color marking at some location on its structure. The drill 50 of matching dimension may also include the same color, such as, for example, the bushing 67 may be of the designated color. Thus, in this system, the surgeon can simply use matching colors to find the correct guide and inserter pair having the selected diameter. Of course, such color marking is particularly useful to a surgeon having a plurality of guides and inserters at his disposal.

In addition to the color marking, this system may further include an additional characteristic to discern between two different sizes of guides and inserters. Specifically, portions of the shaft of the two sizes of inserters may have differing dimensions. In a preferred embodiment, the proximal shaft 22 of the exemplary 1.4 mm inserter 20 may be larger than the proximal shaft 22 of the exemplary 2.3 mm inserter 20. Thus, it would not be possible to use the 1.4 mm inserter (and associated filamentary fixation device 10) with the 2.3 mm cannulated guide. Conversely, the 2.3 mm inserter could not be used with the 1.4 mm cannulated guide because the distal portion 30, distal shaft 24, and filamentary fixation device 10, of the 2.3 mm inserter would be too large to fit through the 1.4 mm cannulated guide.

Additionally, the drill 50 would have similar dimensions to the inserter 20, such that, for example, the proximal portion 63 of the shaft of a 1.4 mm drill would not be capable of fitting into a 2.3 mm cannulated guide. Conversely, the distal tip 61, bushing 67, and potentially even the distal portion 65 of the shaft of a 2.3 mm drill 50 would be too large to fit through a 1.4 mm cannulated guide.

Figure 6A:
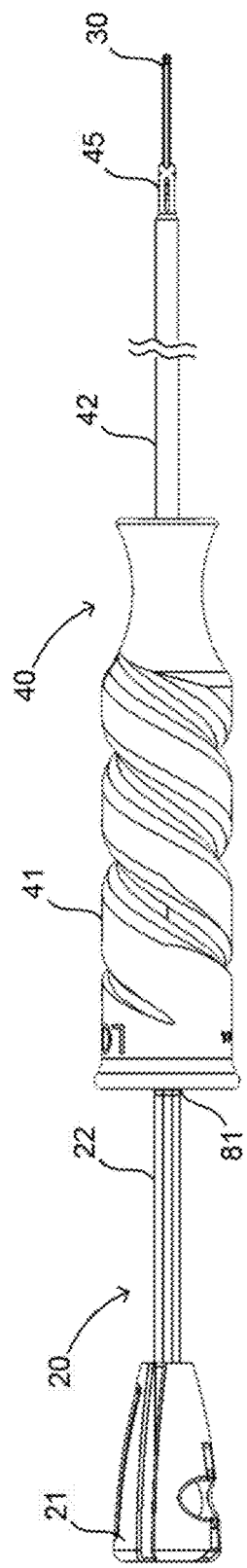
FIGS. 6A and 6B illustrate one arrangement of the cannulated guide of FIGS. 5A-5C and the inserter of FIGS. 3A-3D, where
Figure 6B:
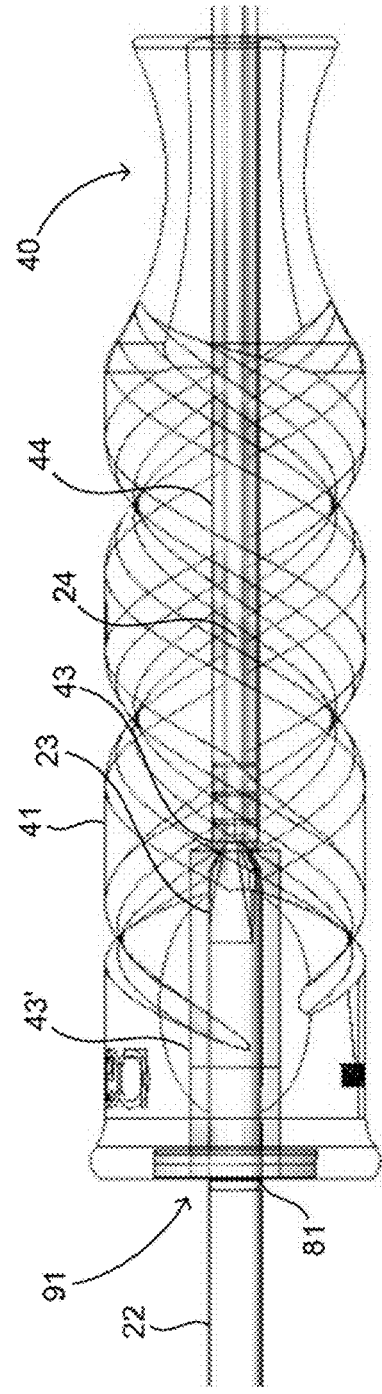

Moreover, this system may have additional features to ensure that certain inserters and drills match with the correct cannulated guides. It should be noted that slotted guides may also be used in this system. For example, as discussed above, the guide may be offered in a variety of lengths, e.g., 5.2 inches and 7.1 inches. For each of the above width dimensions (1.4 mm and 2.3 mm), a single inserter or a single drill may be suitable for use with a guide (having the same width dimension) of either length. For example, as illustrated in FIGS. 6A and 6B, the exemplary cannulated guide 40 may be a 5.2 inch guide. Within the handle, proximal to stop 43, may be positioned a proximal bushing 43' having a diameter sufficient to accommodate the proximal shaft 22 of an inserter 20 (or drill 50). The proximal bushing 43', having this relatively short length, is particularly dimensioned such that the distal portion 30 of inserter 20 protrudes from the distal portion 45 of the guide 50, as illustrated in FIG. 6A. Of course, if the distal portion of the guide were extended as in, for example, the 7.1 inch guide, the distal portion 30 of the inserter may not protrude from the guide at all. Thus, in such an alternative configuration, the proximal bushing of the 7.1 inch guide (not shown) may be longer such that the stop is distal of the position illustrated in FIG. 6B. In some arrangements, the stop may be moved distally a sufficient amount such that the handle 21 is capable of abutting the handle 41 of the guide 50, such that a stop is effectively formed between the two handles (the distal end of handle 21 and the proximal end of handle 41). It is envisioned that the above precaution is still used in these various guides such that, for example, the proximal shaft of a 1.4 mm inserter cannot fit into the proximal end (and proximal bushing) of a 2.3 mm cannulated guide, regardless of whether the guide is of a length of 5.2 inches or 7.1 inches.

As mentioned above, the cannulated guide 40 and drill 50 of this system have similar color markings and shaft sizes, dimensions and stops/shoulders which prevent the surgeon from using the wrong drill with a particular guide. For example, as above, a single drill 50 may be used with either a long or a short guide (though the width dimension must match between the guide and drill, as discussed above). Similar to the inserter 20, the drill 50, when used with the shorter guide, contacts stop 43 with stop or shoulder 66. However, when used with a longer guide, the chuck 62 may contact the proximal end of handle 41. Of course, the shoulder may still contact the stop (now positioned distally within the handle) if the dimensions are so constructed.

In another embodiment, the present invention may include a kit including a plurality of cannulated guides 40 and a plurality of inserters 20. The kit may further include a plurality of drills 50, and further a plurality of bushings 67 for the drill. The bushings may be positioned on the drills, or alternatively, the bushings and drills may be separate and a surgeon can combine a desired drill with a desired bushing. Preferably, each drill has a bushing positioned thereon and the surgeon may need only to select the desired drill (with bushing already attached).

Further as to this embodiment, the plurality of guides may have various inner diameters, of the cannulation 44, various overall lengths, various curves 149 ranging from and including 0 degrees up to and including about 180 degrees, or any combination of these dimensions or other desireable dimensions or features.

Such a kit may also include at least one of the plurality of guides having two curves along its length, such as one curve at a position towards the proximal end of the guide and a second curve, as illustrated throughout, towards the distal end of the guide. Additionally, the plurality of guides may include a plurality of guides having two curves, each of which may have various combinations of first and second curves having different lengths, trajectories and angles, though of course some of such guides may include first and second angles which are themselves the same as compared to one another, but differ from other guides in the kit. The various angles of curvature available may be in set increments, such as in one preferred embodiment, the plurality of guides may include curves of 0 degrees, 12 degrees and 25 degrees. As one example of other features which may be varied within the plurality of guides may concern the distal tip 45, and specifically the shape of the surface 47, such that other arrangements rather than the "crown" shape, or the angled face of surface 247, may be available to the surgeon in this kit.

Continuing with this embodiment, the plurality of inserters 20 may have various width dimensions, various length dimensions, various distal-most end shapes (forked, flat blade, etc.), or any combination. The plurality of drills 50 may also include various width dimensions, various length dimensions, various types and shapes of bushings, and various drill tips 61.

Additionally, this embodiment of the kit may include other devices and instruments such as awls, trocars. The kit may further include at least one filamentary fixation device 10 and at least one loading device 50. The fixation device 10 may be a plurality of fixation devices having various lengths, widths, and the like. For example, as above, the kit may include a device 10 suitable for use with the 1.4 mm instruments and a device 10 suitable for use with the 2.3 mm instruments. The kit may also include at least one filament 15 and at least one threading filament 56*a*. Of course, the above-discussed color markings on the various instruments can be particularly helpful with this type of kit to simplify the selection of the appropriate instruments and devices by the surgeon for a particular surgical application, anatomy, or the like.

In another embodiment, the present invention may include a system, illustrated for example in FIGS. 9A-9C, including a loading device 50, an inserter 20 and a filamentary fixation device 10. The system may be assembled as in FIG. 9B and ready for immediate use (e.g., sterilized and packaged in this configuration). The system may further include at least one threading filament 56*a*, and preferably two threading filaments 56*a*, 56*b*, also assembled with the loading device and filamentary fixation device as illustrated in FIG. 9C, for example. The system may also include a filament 15. The system may also include a cannulated guide 40, 140 and optionally a drill 60.

In yet another embodiment, the present invention may be a kit including a plurality of assemblies, each assembly having a loading device 50, a filamentary fixation device 10, and an inserter 20. Each of the plurality of assemblies may have various characteristics and dimensions from which a surgeon may select the appropriate assembly for a particular surgical application. Various differences between each assembly of the kit may relate to the size or shape of the device 10 (and corresponding inserter 20 size and shape), the path of the channels 54, 55 through the loader and device 10, or other configuration or dimensions as discussed herein. Any of the plurality of assemblies may be used with a filament 15, which also may be included in the kit. The kit may further include pluralities of drills 60 and cannulated guides 40, 140 (or slotted guides) which may be used with the various inserters 20 and devices 10 within the plurality of assemblies.

In yet a further embodiment, the present invention may include a system including a cannulated guide 40, 140 (or alternatively a slotted guide), an inserter 20 and a filamentary fixation device 10. The dimensions of the cannulated guide may be suitable for use with the inserter 20 and filamentary fixation device 10, as discussed in depth above. The system may further include a drill 60, which may include a bushing 67, which is dimensioned for use with the cannulated guide 40, 140.

Any aspect of the above present invention may be disposable or otherwise limited to a single use. For example, the loading device 50 may be disposed after a single use. This is particularly for ease of use purposes, as rethreading the threading filaments 56*a*, 56*b* can be difficult. However, of course, the loading device 50 may be reloadable and reusable by, for example, rethreading the threading filaments 56*a*, 56*b* with the upper case 51*a* removed such that the channels 54, 55 are exposed. The drill 60 may be disposable or reusable, and similarly the bushing 67 may be reusable or reloadable. In one example, the drill may be reusable, but the bushing may be disposable, such that a new bushing must be engaged onto the drill before each use of the drill. The cannulated guide 40 (or slotted guide) may be reusable, though they may also be disposable if so desired. The inserter 20 may also be either reusable or disposable.

In a further embodiment, the present invention may also include a method of loading a filament 15 onto a filamentary fixation device 10, the method including obtaining a first portion 17 having an end 17' and a second portion 18 having an end 18' of the filament 15, positioning ends 17', 18' into filament connectors 56*a'*, 56*b'*, respectively, of threading filaments 56*a*, 56*b* and securing same thereto. The threading filaments 56*a*, 56*b* are positioned within loading device 50, as illustrated for example in FIG. 9C. The opposite ends 56*a"*, 56*b"* of the threading filaments (preferably using loading actuators 59*a*, 59*b*) may then be tensioned, and pulled proximally, by the surgeon, to draw the filament ends 17', 18' into channels 54, 55 and through at least a portion of the device 10. Furthermore, the filament may, prior to engaging the filament with the threading filaments of the loading device, be passed through a tissue, a suture anchor, or both.

In the particular embodiment illustrated in FIG. 9C, for example, each end 17', 18' of the filament 15 may pass first, transversely through device 10 such that the filament passed through a sidewall of the device 10, through the hollow interior 11 and through the opposite sidewall. Upon exiting the sidewall, each end 17', 18' then follows the channels 54, 55 in a generally circular path to one of a first end 12 and a second end 13, and into the hollow interior 11 of the device 10. The ends 17', 18' of the filament, upon passing through the hollow interior, exit from the device 10 from the opposite of the first and second ends 12, 13 from where they entered the device 10. The threading filaments then direct the filament ends 17', 18' through channels 54, 55 until they exit from the loading device on second and third sides 52*b*, 52*c*. The filament portions 17, 18 may then be grasped by the surgeon and the filament ends 17', 18' may be disengaged from the filament connectors 56*a'*, 56*b'*. At this point, the device is loaded with the filament, and, upon removal of the loading actuators 59*a*, 59*b* (if present), the upper and lower casings 51*a*, 51*b* may be separated and the surgeon may grasp handle 21 of the inserter 20. The first and second portions 17, 18 of the filament 15 may be tensioned and secured to the handle, such as by using cleats 26*a*, 26*b* (FIG. 3C). The tensioning of the filament portions may also cause the device to fold over saddle 33 of inserter 20, as illustrated for example in FIG. 4, such that the device 10 now sits within saddle 33 and grooves 32*a*, 32*b*. At this point, the assembly of the inserter 20, device 10 and filament 15 are ready for implantation.

The present invention may also include a variety of surgical methods of repairing soft tissue, preparing a bone for attachment of soft tissue, or for use of the various instruments, devices, kits and systems. What follows are certain exemplary embodiments using various instruments, devices, kits and systems, though of course, other variations to these exemplary methods are also envisioned.

In one embodiment, the present invention includes a method of securing soft tissue to bone. One aspect of such a method is disclosed in FIG. 12, in which the soft tissue 200 is a shoulder labrum which is to be secured to bone 205, specifically, the glenoid. Of course, this specific tissue and bone is for illustrative purposes only, in that this method may be performed on other soft tissue and bone anatomies such as a hip labrum, rotator cuff, or the like. In the example of the repair of a hip labrum, the labrum, in that embodiment, is to be secured to the acetabulum.

Figure 12:
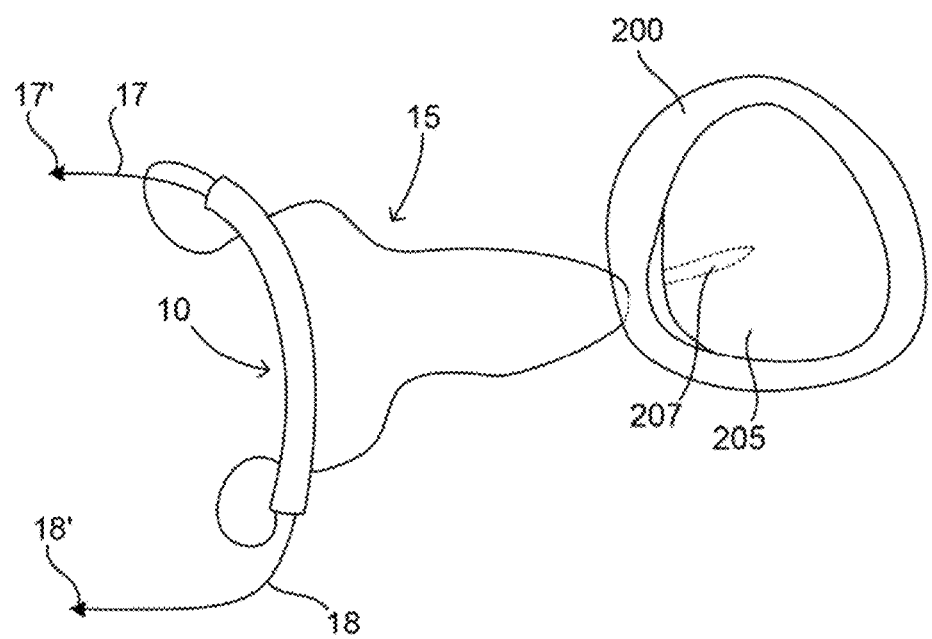
FIG. 12 illustrates one aspect of one embodiment of a method in accordance with the present invention.

In this method of FIG. 12, the soft tissue 200 and bone 205 are accessed via an arthroscopic procedure (though open surgery may alternatively be performed) and filament 15 is passed through the soft tissue 200 such that filament ends 17', 18' extend from the soft tissue. A bore hole 207 may also be prepared in bone 205, into which the filamentary fixation device 10 and at least a portion of the filament 15 will be placed and secured. The ends 17', 18' of the filament 15 may then be loaded, along with filament portions 17, 18, into the filamentary fixation device 10. In practice, the filament 15 may be loaded into device 10 using the loading device 50 (FIGS. 9A-C) as discussed above. Essentially, the filament ends 17', 18' are positioned within filament connectors 56*a'*, 56*b'*, respectively of threading filaments 56*a*, 56*b* and secured thereto. The opposite ends 56*a"*, 56*b"* of the threading filaments (preferably using loading actuators 59*a*, 59*b*) may then be tensioned, and pulled proximally, by the surgeon, to draw the filament ends 17', 18' into channels 54, 55 and through at least a portion of the device 10. As illustrated in FIG. 9C, for example, each end 17', 18' of the filament 15 may pass first, transversely through device 10 such that the filament passed through a sidewall of the device 10, through the hollow interior 11 and through the opposite sidewall. Upon exiting the sidewall, each end 17', 18' then follows the channels 54, 55 in a generally circular path to one of a first end 12 and a second 13, and into the hollow interior 11 of the device 10. The ends 17', 18' of the filament, upon passing through the hollow interior, exit from the device 10 from the opposite of the first and second ends 12, 13 from where they entered the device 10. The threading filaments then direct the filament ends 17', 18' through channels 54, 55 until they exit from the loading device on second and third sides 52*b*, 52*c*. The filament portions 17, 18 may then be grasped by the surgeon and the filament ends 17', 18' may be disengaged from the filament connectors 56*a'*, 56*b'*. At this point, the device is loaded with the filament, and, upon removal of the loading actuators 59*a*, 59*b* (if present), the upper and lower casings 51*a*, 51*b* may be separated and the surgeon may grasp handle 21 of the inserter 20. The first and second portions 17, 18 of the filament 15 may be tensioned and secured to the handle, such as by using cleats 26*a*, 26*b* (FIG. 3C). As illustrated for example in FIG. 4, once the filament 15 is secured to the handle, the device 10 now sits within saddle 33 and grooves 32*a*, 32*b*. At this point, the assembly of the inserter 20, device 10 and filament 15 are ready for implantation.

Using the inserter, the device 10 is then implanted, along with at least a portion of filament 15, into the bore hole 207. Once the implant is positioned within the bore hole, the filament portions 17, 18 may be removed from the handle 21 and the inserter may be removed. Any slack of the filament, between the tissue 200 and the device 10, may be reduced by further tensioning of filament ends 17', 18'. Once the slack is substantially minimized or removed, the filament 15 also tensions the tissue 200 such that the tissue 200 is moved to a position adjacent to or substantially over the bore hole 207. The portions 17, 18 of the filament are then tensioned further, which ultimately results in the device 10 becoming secured within the bore hole, which thereby also secures the filament 15 within the bore hole. Additionally, as the filament 15 is tensioned, the tissue 200 is drawn further to a position substantially adjacent to or on top of the bore hole. The end portions of the filament may be severed, and the access pathway to the surgical site may be closed.

It should be noted that the drilling of the bore hole 207 step may be performed at any time during this method. For example, in one alternative, the bore hole may be prepared first, prior to passing the filament through the tissue 200. Thus, a drill 60 may be passed through a cannulated guide 40, 140 (or slotted guide), and the bore hole prepared. The drill may then be removed from the guide and the steps utilizing the filament 15 and device 10 may then be performed, either through guide 40, 140 or through a surgical cannula or secondary cannulated guide.

Such a method of repair may result in a strong reattachment of the tissue to the bone. The pullout strength of device 10 is at least comparable to conventional anchors, as well as currently available filamentary anchors, such that pullout loads of at least 30 lbs may be capable using device 10.

Figure 13:
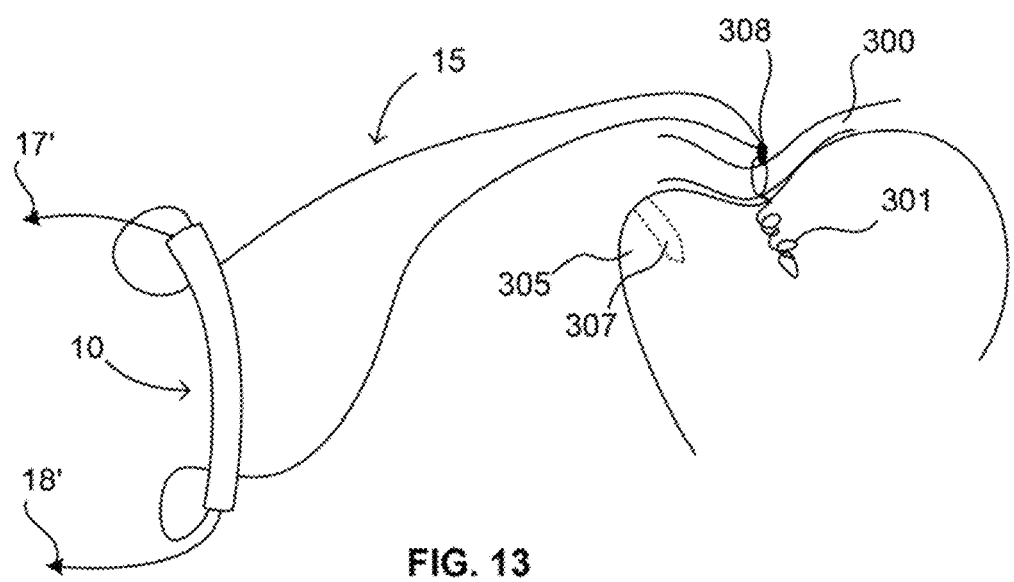
FIG. 13 illustrates one aspect of another embodiment of a method in accordance with the present invention.

Illustrated in FIG. 13 is another embodiment of a method of the present invention, exemplified as a repair of a rotator cuff. Essentially, the method incorporates a "suture bridge" configuration between a medial suture anchor 301, as known in the art, and a lateral anchor in which the filamentary fixation device 10 is used within bore hole 307. In this method, the surgical site is accessed via arthroscopy (though open surgery may alternatively be used), and the medial anchor 301 is implanted under the tissue 300, as is known in the art. The anchor 301 may be implanted through tissue 300 and into bone 305, or alternatively, the tissue 300 may be moved medially and the anchor 301 positioned in the bone 305 without passing through tissue 300. A filament 15 is engaged with the anchor 301 through either a knot or by passing through an eyelet or other structure on anchor 301, such that two end portions 17, 18 of the filament extend from the anchor, terminating in ends 17', 18'. The two end portions are passed through the tissue 300, above the anchor 301 and as illustrated. The two portions 17, 18, extending through the tissue, may optionally form a know 308, above the tissue, to compress a portion of the tissue between the knot and the anchor 301. Alternatively or in addition, the bone anchor 301 may engage the filament 15 such that the filament is fixed to the anchor and may not slide therethrough. The two portions 17, 18 may then be directed laterally over tissue 300 and towards a bore hole 307 which is prepared as discussed above using drill 60. Bore hole 307 may be positioned laterally outside of a native footprint of tissue 300, or alternatively, may be positioned adjacent to or at the edge of the native footprint. Preferably, the bore hole 307 is positioned lateral to the native footprint such that the tissue may be properly tensioned to create an effective repair.

The filament 15 may then be loaded onto the filamentary fixation device 10, as illustrated in FIG. 13, using a similar method as discussed above. Once the filament is loaded, the device 10 and filament 15 are ready for implantation, the steps for which are similar to those above with respect to FIG. 12. Additionally, particularly as to this embodiment, the filament 15 creates a suture bridge over tissue 300 such that the tissue abuts the underlying bone 305 along as much of its surface area of the native footprint as possible.

In one alternative embodiment, the method illustrated in FIG. 13 may be repeated such that two lateral bore holes are formed, two filaments, each having first and second end portions, extend from the medial anchor, and two filamentary fixation devices are used to secure the two filaments within the two bore holes. Such a repair provides for an even larger amount of the surface area of tissue 300 to abut the underlying bone 305. In yet another alternative, the two filaments may extend from two separate medial anchors, such that two separate medial-lateral repairs are performed in parallel. Other such configurations are also envisioned, having varying amounts of medial and lateral anchors and filaments.

Figure 14:
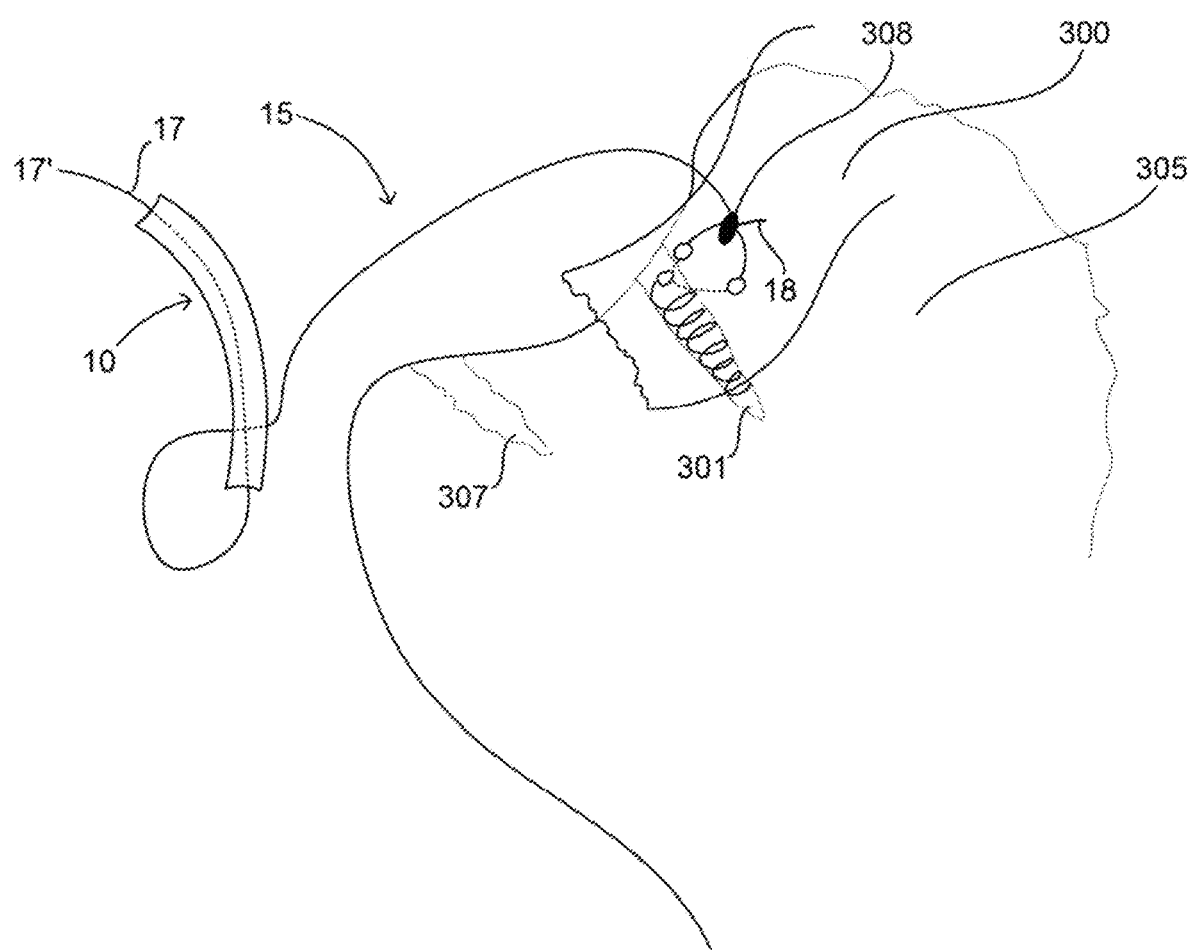
FIG. 14 illustrates one aspect of one embodiment of a method in accordance with the present invention.

In another embodiment, illustrated in FIG. 14, the present invention includes a method, similar to that disclosed in FIG. 13, except that in this embodiment a single filament portion 17, having filament end 17', may be used. The other filament portion 18 may be cut or otherwise removed and not used. As with the embodiment of FIG. 13, in this embodiment, a bone anchor 301 is positioned medially in bone 305, underneath the tissue 300. At least one of the filament portions 17, 18, secured to the anchor 301, is passed through the tissue 30 and positioned over the tissue in a lateral direction. Again, in this example, the tissue 300 is a rotator cuff, though this method may be performed on other soft tissues. If both filament end portions 17, 18 are passed through the tissue, a knot 308 may be formed to provide further securement of the tissue to the bone. A lateral bore hole 307 is also prepared. The end portion 17 of the filament 15 is loaded into filamentary fixation device 10, as discussed above (e.g., using a threading filament 56a (not shown)). The device 10, along with end portion 17 of the filament 15 are then implanted into bone hole 307. The end 17' is then tensioned to secure the filament 15 and device 10 in the bone hole and to tension and draw the rotator cuff laterally towards the later bone hole 307.

Figure 15:
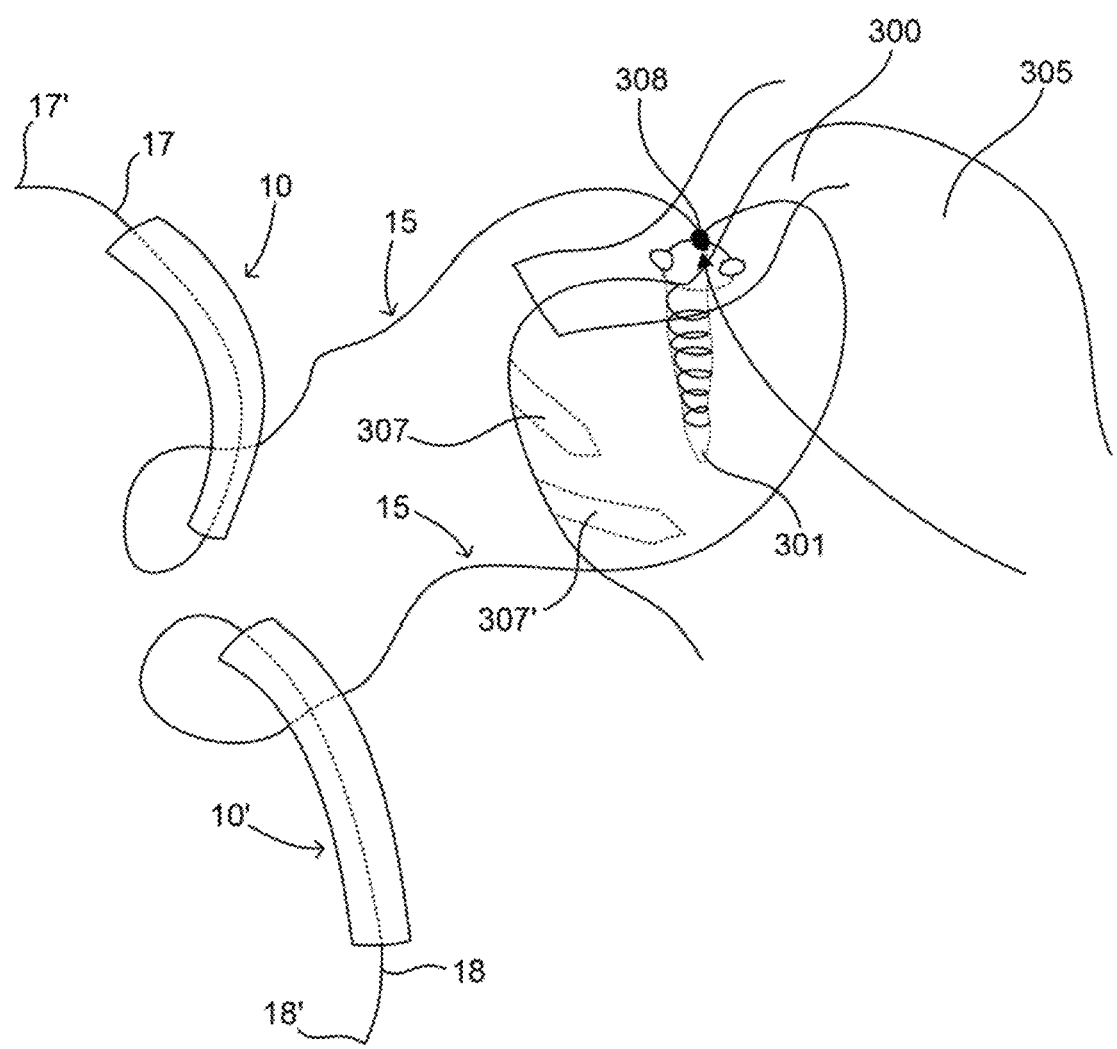
FIG. 15 illustrates one aspect of another method in accordance with the present invention.

FIG. 15 illustrates yet another embodiment of a method of the present invention. In this embodiment, rather than removing or not utilizing the other end portion 18, as in FIG. 14, filament end portion 18 is passed, along with end portion 17, through the tissue 300 (again, using rotator cuff as an example). The end portions 17, 18 may then form knot 308. Both end portions 17, 18 may then be positioned laterally over the tissue. First and second lateral bone holes 307, 307' may be prepared laterally to the tissue. Typically, they are positioned lateral to the native footprint of the, in this example, rotator cuff to provide for lateral tension on the tissue even once the tissue is reattached to its native footprint. As described above, and similar to FIG. 14, the first and second ends 17', 18' are loaded onto first and second filamentary fixation devices 10, 10', respectively. This step is illustrated in FIG. 15. The devices 10, 10' along with end portions 17, 18, respectively, of the filament 15 are then implanted into respective bone holes 307, 307'. The ends 17', 18' are then tensioned to secure the filament 15 and devices 10, 10' in the bone holes and to tension and draw the rotator cuff laterally towards the later bone hole 307.

In another alternative to this embodiment of FIG. 15, the method may include two medial anchors, each having a single filament end portion secured thereto. Each of the filament end portions may then be maneuvered to secure to first and second devices 10, 10', as discussed above, to form a suture bridge repair utilizing four anchors and two lengths of filament. Of course, the filaments may be positioned laterally to the two bone holes such that they form two parallel "bridges," or alternatively, form an "X"-shaped bridge by crossing the filaments prior to implantation of the devices 10, 10' into bone holes 307, 307'.

Figure 16A:
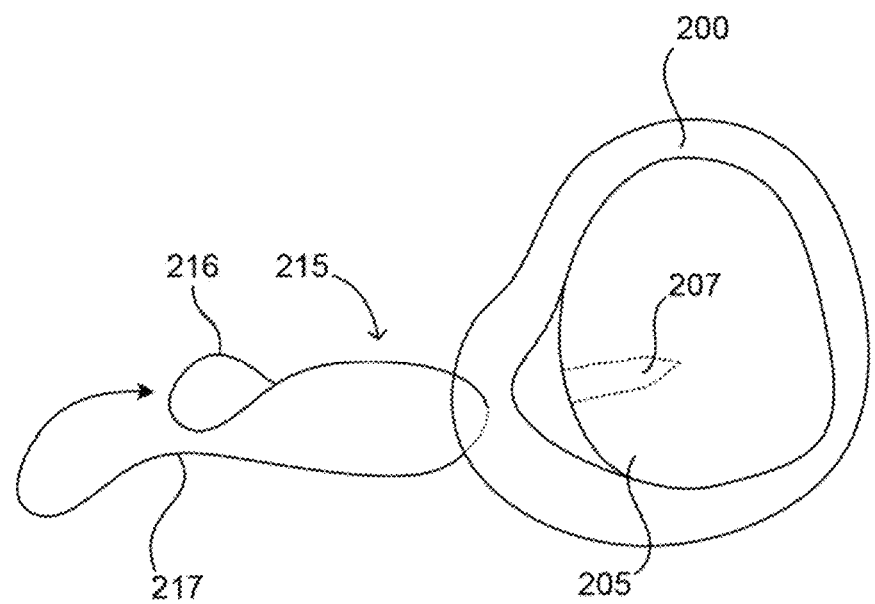
FIGS. 16A and 16B illustrates various steps of yet another embodiment of a method in accordance with the present invention.
Figure 16B:
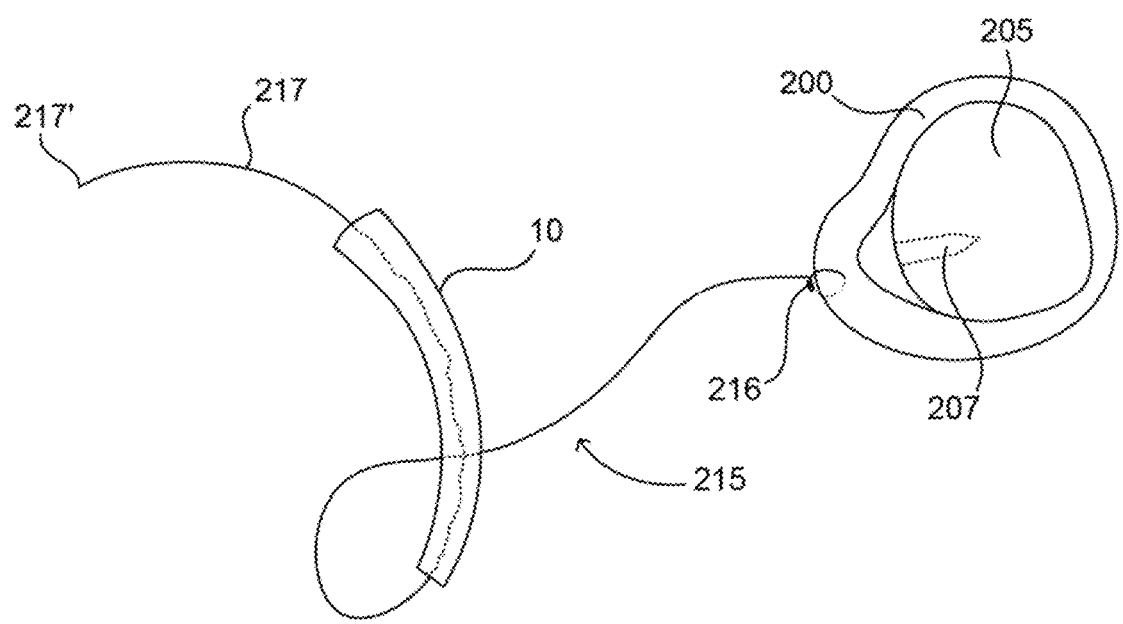

In another embodiment, the present invention may include a method of repairing tissue as is illustrated in FIGS. 16A and 16B. In this embodiment, a filament 215 is used, filament 215 includes a filament portion 217 and a filament end 217' on one side, and a closed loop 216 on the other. Such a filament is used in a tissue repair procedure using a suture anchor in co-pending U.S. application Ser. No. 13/441,290, filed Apr. 6, 2012, owned by the same assignee as the present application, the entirety of which is incorporated by reference herein as if fully set forth herein. In this embodiment, the filament 215 is passed around or through tissue 200, which in this embodiment is exemplified as shoulder labrum tissue. The end portion 217 may then be passed through closed loop 216 and the end portion 217 may be tensioned to form a "luggage tag" configuration, as in FIG. 16B. the device 10 may then be loaded onto the end 217' and end portion 217 of filament 215, as has been discussed in depth above. The device 10, along with end portion 217 of filament 215, may then be implanted into bone hole 207. The end 217' may then be tensioned to secure the device and filament within the bone hole. Such tensioning may also tension the tissue 200 and draw the tissue towards and adjacent to, or over, the bone hole 207. Other variations of this method are also envisioned, for example, utilizing a filament 215 which includes more than one end portion 217 extending from the closed loop 216, such that they may be used in a single device 10, or multiple devices.

In another embodiment, the present invention includes a system for the repair of soft tissue including at least one filament, at least one filamentary fixation device, at least one instrument for insertion of the filament and fixation device, and a surgical procedure. The surgical procedure may include instructions or protocol for using the filament, fixation device, and instrument to repair soft tissue. The protocol may include aspects of any of the above-discussed embodiments, though other variations are also envisioned within the scope of the present invention.

In an associated embodiment, the present invention includes a method of providing instructions or information to practice any of the various methods of performing soft tissue repair described herein. For example, the method may include supplying a surgical protocol, or like document, to provide step-by-step instructions for performing any of the method embodiments of the present invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical instrument comprising:
   an instrument body including:
      a shaft having a distal end, a proximal end, a length therebetween,
      a distal drill tip extending from the distal end,
      a shoulder positioned between the proximal and distal ends, and
      a distal portion extending from a distal end of the shoulder to the distal end of the shaft, the distal portion having a diameter less than a diameter of the shoulder, wherein an entire length of the distal portion is flexible; and
   a bushing including a cannulation extending along a length of the bushing from a proximal end to a distal end, at least one flexible portion along the length having a distal end, and at least one solid portion along the length having a proximal end coupled to the distal end of the flexible portion,
   wherein the distal portion is insertable through the bushing and the distal end of the bushing is configured to compress in a proximal direction such that the distal end of the bushing translates toward the proximal end of the bushing along the length of the distal portion,
   wherein the distal portion is configured during use to be inserted and passed through a curved guide, and
   wherein the bushing has a diameter configured to maintain an entirety of the distal portion surrounded by the bushing in a central location through a curve and after the curve of the curved guide as the distal portion is inserted and passed through the curved guide, such that the distal portion remains substantially coaxial with a longitudinal axis of the curved guide.

2. The surgical instrument of claim 1, the distal end of the bushing is slideable along a portion of the length of the distal portion of the instrument body.

3. The surgical instrument of claim 1, wherein the at least one flexible portion is a spring portion.

4. The surgical instrument of claim 1, wherein the at least one flexible portion comprises a plurality of flexible portions.

5. The surgical instrument of claim 4, wherein each of the flexible portions is separated by a solid portion.

6. The surgical instrument of claim 4, wherein the plurality of flexible portions are spring portions including a first spring portion having a first spring constant and a second spring portion having a second spring constant different from the first spring constant.

7. The surgical instrument of claim 6, wherein when the instrument is in use to form a bore hole, the spring portions compress sequentially.

8. The surgical instrument of claim 1, wherein the bushing and the distal portion of the instrument body are adapted to pass through the curve of the cannulated guide.

9. The surgical instrument of claim 8, wherein the bushing is configured to compress proximally as the bushing moves through the curve of the curved guide.

10. The surgical instrument of claim 1, wherein the bushing is configured to dampen a force exerted proximally by the surgical instrument.

11. The surgical instrument of claim 1, wherein the proximal end of the bushing has an inner diameter to minimize proximal movement of the bushing on the shaft of the instrument body.

12. The surgical instrument of claim 1, wherein the surgical instrument is a drill.

* * * * *